(12) United States Patent
Nguyen et al.

(10) Patent No.: US 12,190,516 B1
(45) Date of Patent: Jan. 7, 2025

(54) COMPUTE SYSTEM WITH THREE-DIMENSIONAL (3D) SKIN DIAGNOSTIC MECHANISM AND METHOD OF OPERATION THEREOF

(71) Applicant: BelleTorus Corporation, Cambridge, MA (US)

(72) Inventors: Tien Dung Nguyen, Toulouse (FR); Thi Thu Hang Nguyen, Toulouse (FR); Pierre Gillibert, Toulouse (FR); Clément Lemeunier, Toulouse (FR); Jérôme Michel Auguste Bertrand, Toulouse (FR)

(73) Assignee: BelleTorus Corporation, Cambridge, MA (US)

( * ) Notice: Subject to any disclaimer, the term of this patent is extended or adjusted under 35 U.S.C. 154(b) by 0 days.

(21) Appl. No.: 18/431,772

(22) Filed: Feb. 2, 2024

(51) Int. Cl.
| | |
|---|---|
| *G06T 7/00* | (2017.01) |
| *A61B 5/00* | (2006.01) |
| *G06T 7/12* | (2017.01) |
| *G06T 17/20* | (2006.01) |
| *G16H 50/20* | (2018.01) |

(52) U.S. Cl.
CPC .......... *G06T 7/0012* (2013.01); *A61B 5/441* (2013.01); *G06T 7/12* (2017.01); *G06T 17/20* (2013.01); *G16H 50/20* (2018.01); *G06T 2207/20084* (2013.01); *G06T 2207/30088* (2013.01)

(58) Field of Classification Search
CPC ......... G06T 7/0012; G06T 7/12; G06T 17/20; G06T 2207/20084; G06T 2207/30088; A61B 5/441; G16H 50/20
See application file for complete search history.

(56) References Cited

U.S. PATENT DOCUMENTS

| | | |
|---|---|---|
| 9,504,420 B2 | 11/2016 | Davis et al. |
| 10,169,541 B2 | 1/2019 | Apte et al. |
| 11,508,168 B2 | 11/2022 | Allen et al. |
| 2015/0003699 A1 | 1/2015 | Davis et al. |
| 2017/0228514 A1 | 8/2017 | Apte et al. |
| 2020/0016003 A1 | 1/2020 | Boncyk et al. |
| 2020/0032111 A1 | 1/2020 | Ogawa et al. |
| 2020/0160032 A1 | 5/2020 | Allen et al. |
| 2020/0234444 A1* | 7/2020 | Budman ............... G06T 7/0016 |
| 2020/0302608 A1* | 9/2020 | Kaffenberger .......... G06N 3/08 |
| 2020/0321115 A1 | 10/2020 | Neumann |
| 2021/0345942 A1* | 11/2021 | Kinsler ..................... G06T 7/50 |

OTHER PUBLICATIONS

Ahmedt-Aristizabal et al. "Monitoring of Pigmented Skin Legions Using 3D Whole Body Imaging." Computer Methods and Programs in Biomedicine, 232, 2023, pp. 1-17 (Year: 2023).*

* cited by examiner

*Primary Examiner* — Jon Chang

(74) *Attorney, Agent, or Firm* — Perspectives Law Group, Corp.

(57) ABSTRACT

A method of operation of a compute system includes: generating a digital model from a input image; segmenting a 3D-polygon from the input image by applying a triangular mesh; assembling a 3D surface, based on the digital model of a zone of interest from the 3D-polygon; calculating an average threshold value of pixels within the zone of interest for identifying a condition over the 3D surface; and assembling a skin condition display from analyzing by a skin artificial intelligence (AI) of the 3D surface for displaying on a device.

20 Claims, 7 Drawing Sheets
(4 of 7 Drawing Sheet(s) Filed in Color)

COMPUTE SYSTEM WITH THREE-DIMENSIONAL (3D) SKIN DIAGNOSTIC MECHANISM AND METHOD OF OPERATION THEREOF

TECHNICAL FIELD

An embodiment of the present invention relates generally to a compute system, and more particularly to a system with a 3D skin diagnostic mechanism.

BACKGROUND

Dermatologists rely on extensive experience to refine their accuracy. In many cases experienced dermatologists do not agree when analyzing the same images of a patient. The early detection of skin conditions can significantly impact the patient's recovery. It also requires accuracy to document the evolution of a lesion or evaluate the efficacy of a treatment. Most classical measurement methods are based on visual estimation by a doctor. However, such methods have to be rather simple and cannot be very precise.

Thus, a need still remains for a compute system with a 3D skin diagnostic mechanism to provide an accurate measurement of lesions to assist healthcare professionals. In view of the ever-increasing commercial competitive pressures, along with growing healthcare needs, healthcare expectations, and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

An embodiment of the present invention provides a method of operation of a compute system including: generating a digital model from a input image; segmenting a 3D-polygon from the input image by applying a triangular mesh; assembling a 3D surface, based on the digital model of a zone of interest from the 3D-polygon in the input image; calculating an average threshold value of pixels within the zone of interest for identifying an acne over the 3D surface; and assembling a skin condition display from analyzing by a skin artificial intelligence (AI) of the 3D surface for displaying on a device.

An embodiment of the present invention provides a compute system, including a control circuit, including a processor, configured to generate a digital model from a input image; segment 3D-polygons from the input image by a triangular mesh; assemble a 3D surface, based on the digital model of a zone of interest from the 3D-polygons in the input image; and calculate an average threshold value of pixels within the zone of interest to identify an acne over the 3D surface; and a communication circuit, coupled to the control circuit, configured to: transfer a skin condition display from a skin artificial intelligence (AI) analysis of the 3D surface for displaying on a device.

An embodiment of the present invention provides a non-transitory computer readable medium including instructions for a compute system, including: generating a digital model from a input image; segmenting a 3D-polygon from the input image by applying a triangular mesh; assembling a 3D surface, based on the digital model of a zone of interest from the 3D-polygon in the input image; calculating an average threshold value of pixels within the zone of interest for identifying an acne over the 3D surface; and assembling a skin condition display from analyzing by a skin artificial intelligence (AI) of the 3D surface for displaying on a device.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
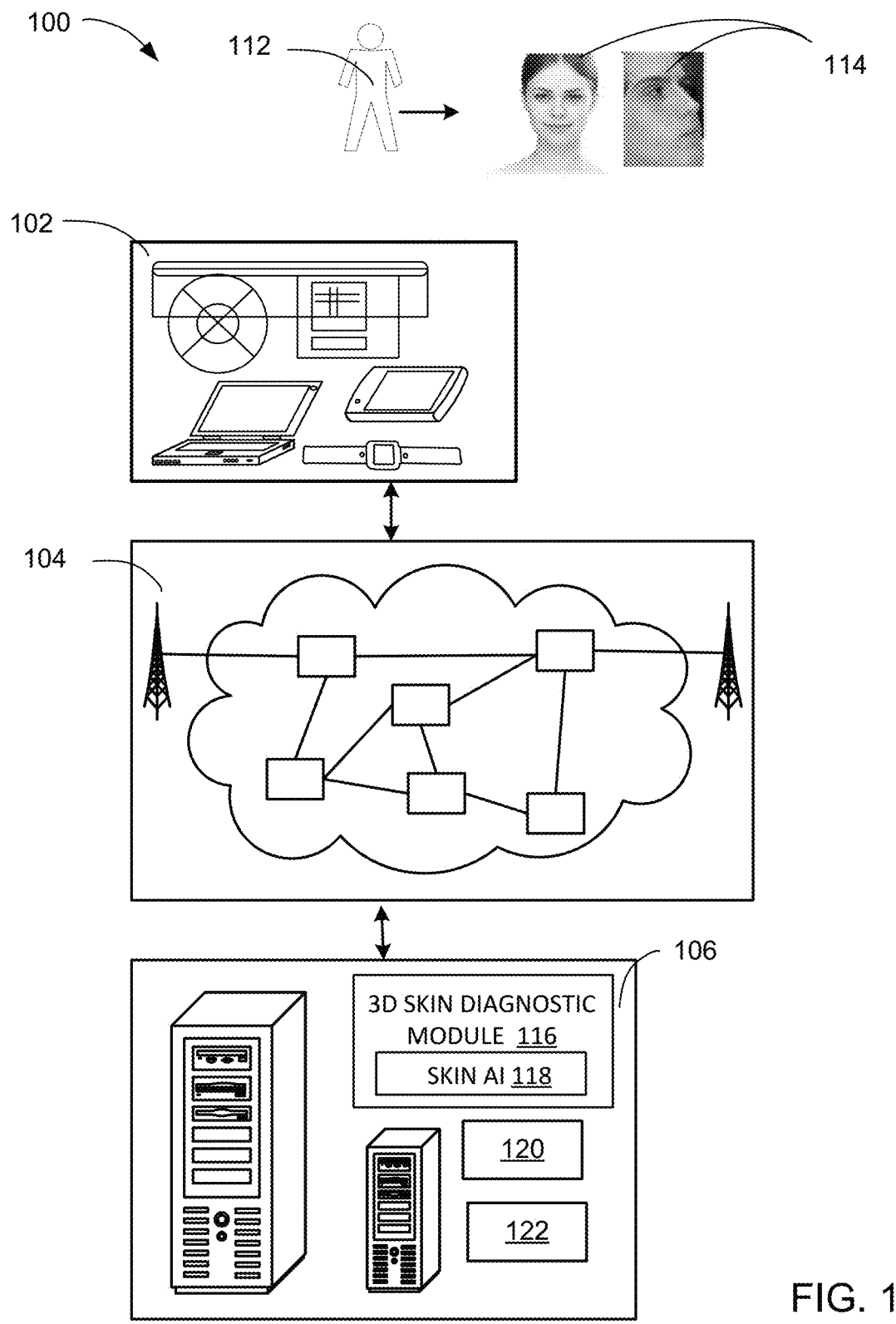
FIG. 1 is an example of a system architecture diagram of a compute system with a three-dimensional (3D) skin diagnostic mechanism in an embodiment of the present invention.

Acne vulgaris (acne for short) consistently represents the top three most prevalent skin conditions in the general population in the world. Due to lack of knowledge or disregard for acne, or lack of means (time and money and doctors), many people with acne do not get a proper treatment. Acne vulgaris can lead to severe irritation, ugly long-lasting scars (about 10% of population have acne scars), and other issues if not diagnosed and treated correctly.

There are several applications of artificial intelligence (AI) used to segment lesions on pictures, and estimate the (point-wise) severity. A simple average can be used to estimate the global severity. However, such method is limited. Different pixel on a picture might not represent the same surface on the body, in other word a projection does not preserve surface proportions. So, this simple average method can overestimate or underestimate the importance of a lesion. A second related problem is that when we have several pictures, we get an estimate per picture and not a global estimate.

There are two common methods for acne severity assessment: counting and grading. Acne counting is a challenging job since normally acne is a small mark and has similar color to skin. Grading is the comparison between some descriptions or photos. Grading methods can be easy to use but can be inconsistent among doctors since it is a subjective method.

A method to correct the average of severity, and to (virtually) fuse together the images to obtain only one consistent global severity is the goal of this disclosure. In addition, this method works even if the severity annotations are inconsistent, due to measurement errors for example. The description thus far has been about pictures with skin lesions, but the same method might be applied for many different purposes. Whenever several picture of an object are provided, the method can measure a value of a function on the picture, then an estimate of the average value over the object can be generated.

As mentioned above, doctors can miss some acne during their annotation process. If an artificial intelligence (AI) model or machine learning (ML) model learn or are trained with those images, the images with the missed annotation will create a confusion and inconsistency (because of non-labeled acne, the AI/ML model will learn or be trained that the missed annotated images are not acne when those images should be labeled as acne).

Embodiments of the compute system with a 3D skin diagnostic mechanism provide more consistent and accurate acne scoring and classifies different types of acne for diagnostics at least by recognizing multiple acne in a given image and assessing each while other often miss acne locations as well as limit the number of acne in a given image. As examples of embodiments, the compute system with the 3D skin diagnostic mechanism can identify, segment, or a combination thereof all or multiple acne and acne-like on a given image. Continuing with the example, the identification and segmentation can be implemented by a segmentation model or module, which will be described more later. Embodiments of the compute system with the 3D skin diagnostic mechanism do not need doctors to do this work and avoiding some of the challenges as noted above. Further, embodiments eliminate or reduce the probability of missing acne.

Continuing with examples of embodiments, the compute system with the 3D skin diagnostic mechanism can perform segmentation, generating more precise results than bounding boxes for identifying acne and pores in the skin. Further continuing the examples, the compute system with the 3D skin diagnostic mechanism can classify the detected acne. The compute system with the 3D skin diagnostic mechanism can utilize annotated data from doctors as input as labeled data to training the AI/ML models of the compute system with the 3D skin diagnostic mechanism and can compensate for the missing acne annotation by the doctors leading to solving the inconsistency problem.

The compute system with the 3D skin diagnostic mechanism can utilize acne counting, acne scoring, and acne segmentation to compute area of each acne, without requiring training for the area calculation of each acne. The compute system with the 3D skin diagnostic mechanism process through acne area calculation for each acne provide consistent results for diagnostics. Continuing the examples for embodiments, the compute system with the 3D skin diagnostic mechanism generates a severity from 0 to 100, which is precise or objective value while also being sensitive in the changing of number of acne and each of its severity. The consistent and accurate scoring as well as the acne area computation from the compute system with the 3D skin diagnostic mechanism can also be utilized to track the progress of treatment.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments of various components as a matter of descriptive convenience and are not intended to have any other significance or provide limitations for an embodiment of the present invention.

The term "module" or "unit" or "circuit" referred to herein can include or be implemented as or include software running on specialized hardware, hardware, or a combination thereof in the present invention in accordance with the context in which the term is used. For example, the software can be machine code, firmware, embedded code, and application software. The software can also include a function, a call to a function, a code block, or a combination thereof. The word "module" or "model" can be also be used interchangeable depending on the context it is described or used in the written description. The "model" can represent one or more artificial intelligence models, machine learning models, or a combination thereof. The term "acne pimples" referred to herein means any type of acne including white heads, black heads, pustules, cysts, nodules, papules, comedones, or discolorations, without limitation.

Also, for example, the hardware can be gates, circuitry, processor, computer, integrated circuit, integrated circuit cores, memory devices, a pressure sensor, an inertial sensor, a microelectromechanical system (MEMS), passive devices, physical non-transitory memory medium including instructions for performing the software function, a portion therein, or a combination thereof to control one or more of the hardware units or circuits. Further, if a "module" or "unit" or a "circuit" is written in the claims section below; the "unit" or the "circuit" is deemed to include hardware circuitry for the purposes and the scope of the claims.

The module, units, or circuits in the following description of the embodiments can be coupled or attached to one another as described or as shown. The coupling or attachment can be direct or indirect without or with intervening items between coupled or attached modules or units or circuits. The coupling or attachment can be by physical contact or by communication between modules or units or circuits, such as wireless communication.

The word "module" or "model" can be also be used interchangeable depending on the context it is described or used in the written description. The "model" can represent one or more artificial intelligence models, machine learning models, or a combination thereof. It is understood the models identified in the description can be operated concurrently, in sequence, or in alternative without changing the operation of the models.

It is also understood that the nouns or elements in the embodiments can be described as a singular instance. It is understood that the usage of singular is not limited to singular but the singular usage can be applicable to multiple instances for any particular noun or element in the application. The numerous instances can be the same or similar or can be different.

Referring now to FIG. 1, therein is shown an example of a system architecture diagram of a compute system 100 with a 3D skin diagnostic mechanism in an embodiment of the present invention. Embodiments of the compute system 100 provide standardized and objective acne scoring and area calculation for each of the acne, as described earlier.

The compute system 100 can include a first device 102, such as a client or a server, connected to a second device 106, such as a client or server. The first device 102 can communicate with the second device 106 through a network 104, such as a wireless or wired network.

For example, the first device 102 can be of any of a variety of computing devices, such as a smart phone, a tablet, a cellular phone, personal digital assistant, a notebook computer, a wearable device, internet of things (IoT) device, or other multi-functional device. Also, for example, the first device 102 can be included in a device or a sub-system.

The first device 102 can couple, either directly or indirectly, to the network 104 to communicate with the second device 106 or can be a stand-alone device. The first device 102 can further be separate form or incorporated with a vehicle, such as a car, truck, bus, motorcycle, or a drone.

For illustrative purposes, the compute system 100 is described with the first device 102 as a mobile device, although it is understood that the first device 102 can be different types of devices. For example, the first device 102 can also be a non-mobile computing device, such as a server, a server farm, cloud computing, or a desktop computer.

The second device 106 can be any of a variety of centralized or decentralized computing devices. For example, the second device 106 can be a computer, grid computing resources, a virtualized computer resource, cloud computing resource, routers, switches, peer-to-peer distributed computing devices, or a combination thereof.

The second device 106 can be centralized in a single room, distributed across different rooms, distributed across different geographical locations, embedded within a telecommunications network. The second device 106 can couple with the network 104 to communicate with the first device 102. The second device 106 can also be a client type device as described for the first device 102.

For illustrative purposes, the compute system 100 is described with the second device 106 as a non-mobile computing device, although it is understood that the second device 106 can be different types of computing devices. For example, the second device 106 can also be a mobile computing device, such as notebook computer, another client device, a wearable device, or a different type of client device.

Also, for illustrative purposes, the compute system 100 is described with the second device 106 as a computing device, although it is understood that the second device 106 can be different types of devices. Also, for illustrative purposes, the compute system 100 is shown with the second device 106 and the first device 102 as endpoints of the network 104, although it is understood that the compute system 100 can include a different partition between the first device 102, the second device 106, and the network 104. For example, the first device 102, the second device 106, or a combination thereof can also function as part of the network 104.

The network 104 can span and represent a variety of networks. For example, the network 104 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path. Ethernet, digital subscriber line (DSL), fiber to the home (FTTH), and plain old telephone service (POTS) are examples of wired communication that can be included in the network 104. Further, the network 104 can traverse a number of network topologies and distances. For example, the network 104 can include direct connection, personal area network (PAN), local area network (LAN), metropolitan area network (MAN), wide area network (WAN), or a combination thereof.

Returning to the description, standardized and objective acne scoring of the embodiments of the compute system 100, as an example, the compute system 100 provide functions to various users 112, including patients and clinicians. The compute system 100 can provide functions to the users 112 in a number of ways.

For example, the compute system 100 can provide the functions for the users 112 with the first device 102, the second device 106, distributed between these two devices, or a combination thereof. Also as examples, the compute system 100 can provide a mobile applications for the patients, the clinicians, or a combination thereof. Further as an example, the compute system 100 can provide the functions via a web-browser based applications or a software to be executed on the first device 102, the second device 106, distributed between these two devices, or a combination thereof.

In one embodiment as an example, input images 114 are taken and uploaded by the patient and reviewed by the clinician. In this embodiment, a patient launches the 3D skin diagnostic mechanism via the mobile application and logs into the patient's account. The patient can be prompted to upload or take body images as the input images 114. The compute system 100 can guide a patient on photo guidelines for the input images 114 and accepts or rejects the input images 114 for retake based on a pre-specified criteria, e.g., distance, quality, blur, or a combination thereof. The compute system 100 can also provide guides for a patient on capturing videos as opposed to still photos. The input images 114 can be selected from the video.

Once the input images 114, as required for analysis, are successfully uploaded, the compute system 100 can send or load the input images 114 to a three-dimensional (3D) skin diagnostic module 116 for analysis including a skin artificial intelligence (AI) 118. The 3D skin diagnostic module 116 will be described later. For brevity and clarity and as an example, the 3D skin diagnostic module 116 is shown in FIG. 1 as being executed in the second device 106 although it is understood that portions can operate on the first device 102, such as the mobile app or the web-browser based application, can operate completely on the first device 102, or a combination thereof. As a further example, the 3D skin diagnostic module 116 can be implemented in software running on specialized hardware, full hardware, or a combination thereof.

The skin AI 118 can be software executed on a processor, core, ASIC, specialized GPU, or a combination thereof configured as a machine learning structure. The combination of hardware decision nodes including for example gates and switches combined with a machine learning software that can process the input images 114 at a pixel level.

Based on analysis results, the compute system 100 can display information to the patient including a recommendation based on the input images 114, uploaded, for the patient to schedule a visit with your primary care physician or with a specialist based on an acne indication 120, which may or may not be visible or displayed to the patient.

If the 3D skin diagnostic module 116 provides the acne indication 120 below a pre-specified threshold 122, the compute system 100 can display a message that based on the input images 114, uploaded, the patient may not need a visit with your primary care physician or with other specialists. The compute system 100 can provide a function allowing the patient to schedule a visit with the clinician.

Continuing the example, the compute system 100 can provide a function that allows the clinician to access the input images 114 uploaded by the patient and an acne indication 120, such as the acne score, the acne area, or a combination thereof through the web-based dashboard from the 3D skin diagnostic mechanism. The compute system 100 allows the clinician to make edits to annotations determined by the 3D skin diagnostic module 116 and the scores (if necessary) and saves the results. The clinician can utilize the acne indication 120 to make the diagnostic decision and provide necessary treatment steps (if applicable).

In a further embodiment as an example, the compute system 100 can allow a patient to schedule a visit with a primary care physician or with a specialist. A clinician can launch the 3D skin diagnostic mechanism, such as a mobile application and logs in. The compute system 100 can be prompted to upload or take the input images 114 of the patient's body or body parts to be analyzed by the 3D skin diagnostic module 116.

The compute system 100 can provide guidance to the clinician on the photo guidelines. The compute system 100 can accept or reject images for retake based on a pre-specified criteria, such as distance, quality, blur, or a combination thereof. Once the input images 114 are successfully uploaded, the compute system 100 and send or load the input images 114 to the 3D skin diagnostic module 116 for analysis.

Continuing the example, the compute system 100 can similarly provide a function that allow the clinician to access the input images 114 uploaded by the patient and the acne indication 120, such as with the web-based dashboard from the 3D skin diagnostic mechanism. The compute system 100 allows the clinician to make edits to annotations determined by the 3D skin diagnostic module 116 and the scores (if necessary) and saves the results. The clinician can utilize the acne indication 120 to make the diagnostic decision and provide necessary treatment steps (if applicable).

Figure 2:
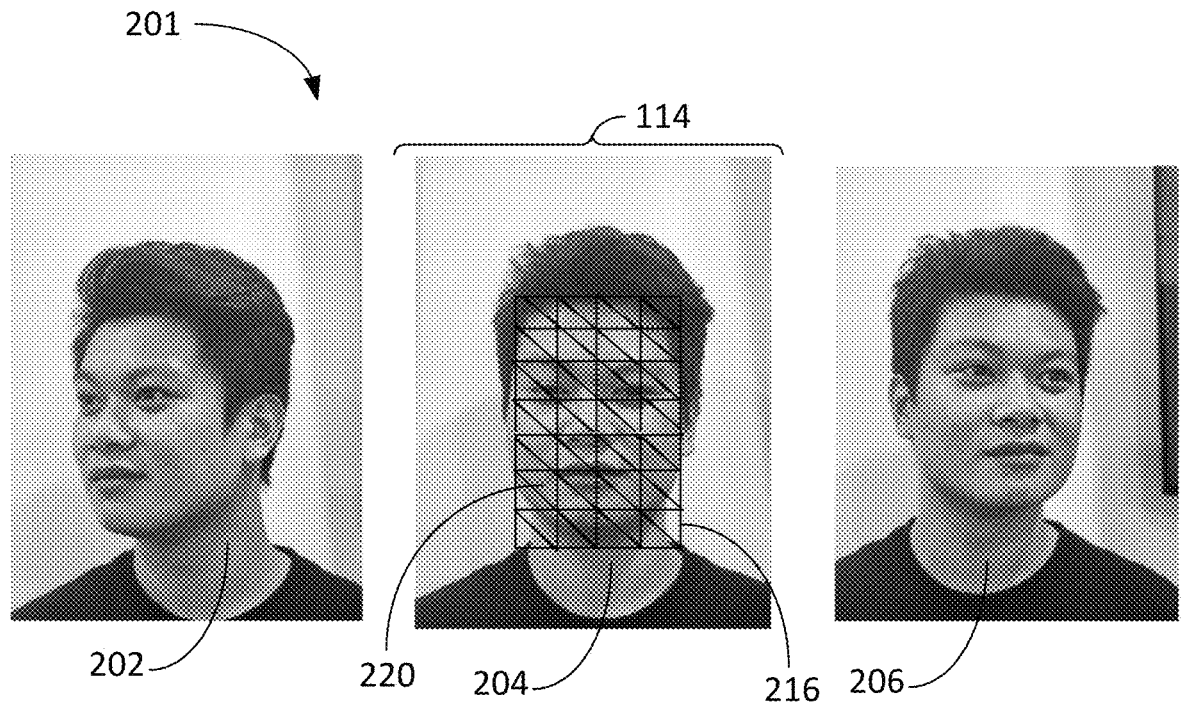
FIG. 2 is an exemplary combination of input images submitted to the 3D skin diagnostic module in an embodiment.
Figure 2:
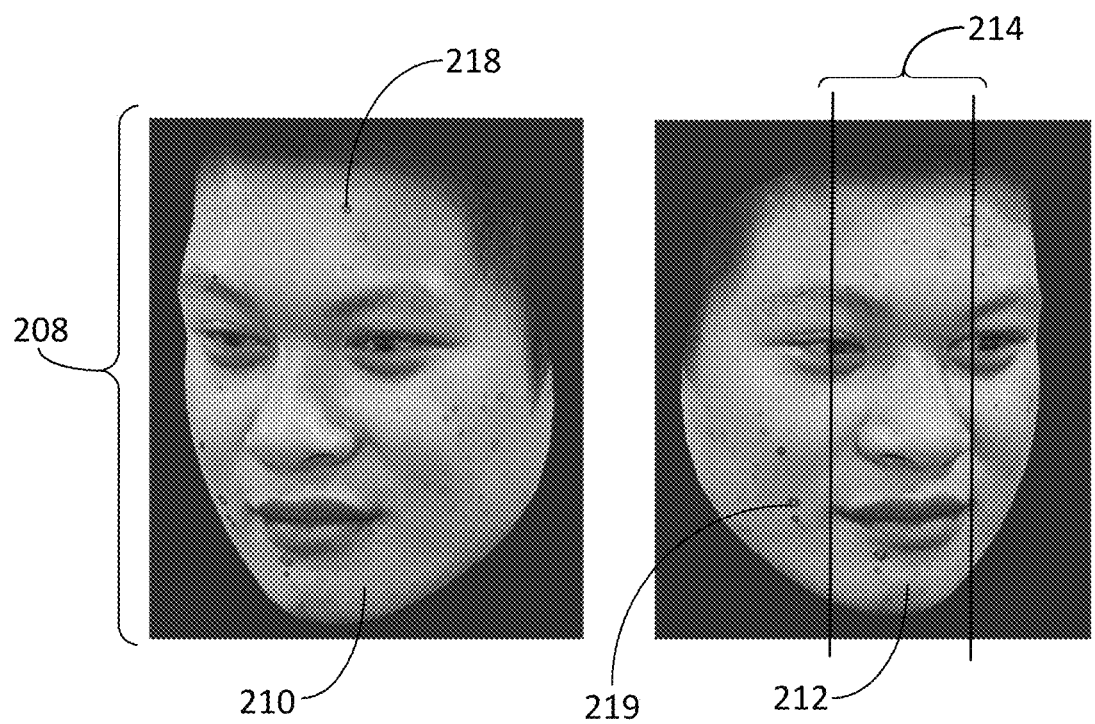

Referring now to FIG. 2, therein is shown an exemplary combination 201 of input images 114 submitted to the 3D skin diagnostic module 116 in an embodiment. The compute system 100 of FIG. 1, the 3D skin diagnostic module 116 of FIG. 1, or a combination thereof can process the input images 114, such as a left side image 202, a central image 204, and a right side image 206. The 3D skin diagnostic module 116 can accept the left side image 202, the central image 204, and the right side image 206 for processing a 3D image sequence 208.

When the left side image 202, the central image 204, and the right side image 206 are processed individually, they can represent incorrect ranges of detection of the skin conditions based on lighting, contrast, focus, and shadows caused by the contour of the surface represented in the input images 114. Some of the skin conditions visible in more than one of the input images 114 can be resolved to be the same occurrence of the skin condition.

The 3D image sequence 208 can include a first hemisphere image 210) and a second hemisphere image 212. Before merging the left side image 202, the central image 204, and the right side image 206, each can have a different threshold for detection of the skin condition based on the differences in contrast, shadowing, luminosity, focus, distance differences, or a combination thereof.

The 3D image sequence 208 can be assembled by pixel matching of the input images 114. The generation of the 3D image sequence 208 allows definition of a single set of thresholds that apply to the entire 3D surface. By way of an example, the first hemisphere image 210 and the second hemisphere image 212 can have an overlap region 214 that is common to both. The overlap region 214 can be the reference for adjusting the thresholds used in the entire area of the first hemisphere image 210 and the second hemisphere image 212.

A triangular mesh 216 can be applied to the left side image 202, the central image 204, and the right side image 206 for processing the 3D image sequence 208. The triangular mesh 216 allows the left side image 202, the central image 204, and the right side image 206 to be segmented for analysis of the triangles allows for assembly of the 3D image sequence 208 and generation of common thresholds for analysis by the skin AI 118 of FIG. 1. By way of an example, the left side image 202, the central image 204, and the right side image 206 can be compared pixel by pixel in order to generate the 3D image sequence 208. It is understood that the triangular mesh 216 can be of any size to cover the maximum area of the input images 114 for identifying a size and location of a condition 218 consistently across the 3D image sequence 208. The condition 218, such as acne, can be identified by an identifying marker 219, such as a highlighted circle positioned around the area of the condition 218. The analysis of the input image 114 covered by the triangular mesh 216 is described in a later section. The triangular mesh 216 is composed of a plurality of 3D-polygons 220, such as triangles that subdivide the input image 114 into multiple smaller regions that can be analyzed and averaged across the entire surface of the 3D image sequence 208 in order to assess the concentration of the condition 218.

By way of an example, a comparison of the left side image 202, the central image 204, and the right side image 206 analyzed individually as compared to the analysis of the 3D image sequence 208 is shown below in Table one:

| IMAGE | NO. COMEDO | NO. PAPULE POSTULE | NO. NODULE CYST | SEVERITY |
| --- | --- | --- | --- | --- |
| LEFT | 26 | 1 | 0 | 1 |
| RIGHT | 21 | 5 | 0 | 4 |
| FRONT | 13 | 4 | 0 | 3 |
| 3D RESULT | 22 | 7 | 0 | 5.95 |

As shown in Table one, it is understood that the result of analysis of the skin AI 118 on the 3D image sequence 208 is slightly superior to the analysis of the left side image 202, the central image 204, and the right side image 206 individually.

It has been discovered that the combination of the input images 114 to form the first hemisphere image 210 and the second hemisphere image 212 can enhance the detection of the skin condition. The 3D image sequence 208 provides a consistent indication of the skin condition under analysis across the set of the input images 114. This enhancement can provide the ability to monitor the progress of treatment as well as the comparison of different lesions in the first hemisphere image 210 and the second hemisphere image 212.

Figure 3:
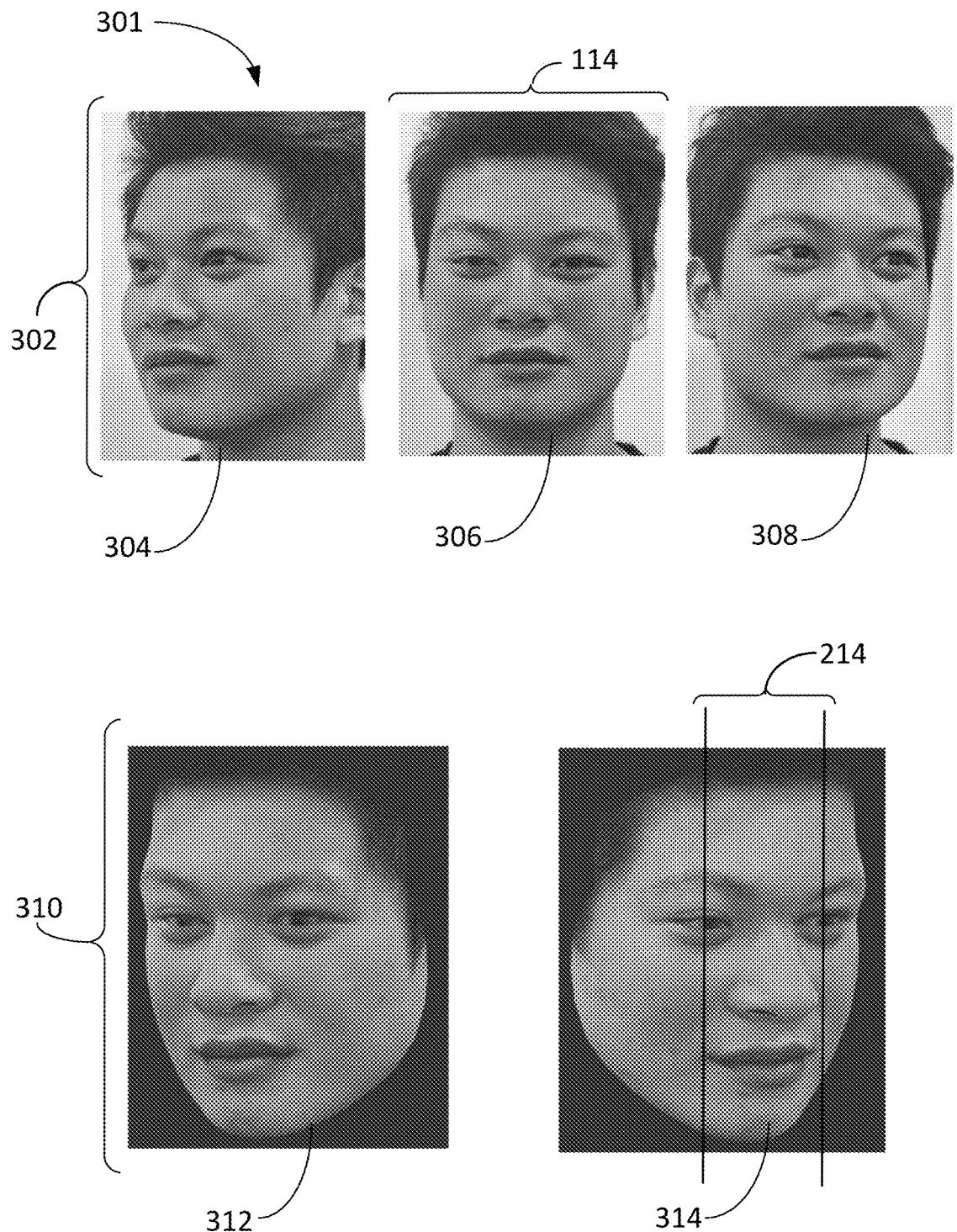
FIG. 3 is an exemplary combination of input images with heat maps submitted to the 3D skin diagnostic module in an embodiment.

Referring now to FIG. 3, therein is shown an exemplary combination 301 of input images 114 with heat maps 302 submitted to the 3D skin diagnostic module 116 in an embodiment. The compute system 100 of FIG. 1, the 3D skin diagnostic module 116 of FIG. 1, or a combination thereof can process the input images 114, such as a left side heat map 304, a central heat map 306, and a right side heat map 308. The 3D skin diagnostic module 116 can accept the left side heat map 304, the central heat map 306, and the right side heat map 308 for processing a 3D heat map sequence 310.

The heat map 302 is an image with pixels in one-to-one correspondence with another image (i.e. they have the same dimensions). The values of the heat map 302 corresponds to properties of the image (or the object on the image). For example, we can have a picture of someone and the heat map 302 indicating which pixels are aggravated pores in the skin.

When the left side heat map 304, the central heat map 306, and the right side heat map 308 are processed individually they can represent incorrect ranges of detection of the skin conditions based on lighting, contrast, focus, and shadows caused by the contour of the surface represented in the input images 114. Some of the skin conditions visible in more than one of the input images 114 can be resolved to be the same occurrence of the skin condition.

The 3D heat map sequence 310 can include a first hemisphere heat map 312 and a second hemisphere heat map 314. Before merging the left side heat map 304, the central heat map 306, and the right side heat map 308, each can have a different threshold for detection of the skin condition based on the differences in contrast, shadowing, luminosity, focus, distance differences, or a combination thereof.

The 3D heat map sequence 310 can be assembled by pixel matching of the input images 114. The generation of the 3D heat map sequence 310 allows definition of a single set of thresholds that apply to the entire 3D surface. By way of an example, the first hemisphere heat map 312 and the second hemisphere heat map 314 can have the overlap region 214 that is common to both. The overlap region 214 can be the reference for adjusting the thresholds used in the entire area of the first hemisphere heat map 312 and the second hemisphere heat map 314.

By way of an example, the skin AI 118 of FIG. 1 can be used to analyze the pore sizes based on the heat maps 302. The estimation of scores on the left side heat map 304, the central heat map 306, and the right side heat map 308 can show variations that are resolved by the analysis of the first hemisphere heat map 312 and the second hemisphere heat map 314.

| IMAGE | CHIN | RIGHT CHEEK | LEFT CHEEK | FOREHEAD | SEVERITY |
| --- | --- | --- | --- | --- | --- |
| LEFT | 22.0 | NAN | 27.5 | 21.9 | 23.9 |
| RIGHT | 22.6 | 26.6 | NAN | 18.8 | 21.8 |
| FRONT | 23.9 | 33.4 | 30.0 | 21.3 | 25.5 |
| 3D RESULT | 23.18 | 24.74 | 25.95 | 18.73 | 22.58 |

As demonstrated by Table two above, the analysis of the pore size as performed by the skin AI 118 of FIG. 1 is slightly lower on the first hemisphere heat map 312 and the second hemisphere heat map 314 than the analysis of the left side heat map 304, the central heat map 306, and the right side heat map 308 individually. This can demonstrate that the common thresholds generated across the first hemisphere heat map 312 and the second hemisphere heat map 314 can provide a less severe and more accurate response.

It has been discovered that the combination of the input images 114 to form the first hemisphere heat map 312 and the second hemisphere heat map 314 can enhance the detection of the skin condition. The 3D heat map sequence 310 provides a consistent indication of the skin condition under analysis across the set of the input images 114. This enhancement can provide the ability to monitor the progress of treatment as well as the comparison of different lesions in the first hemisphere heat map 312 and the second hemisphere heat map 314.

Figure 4:
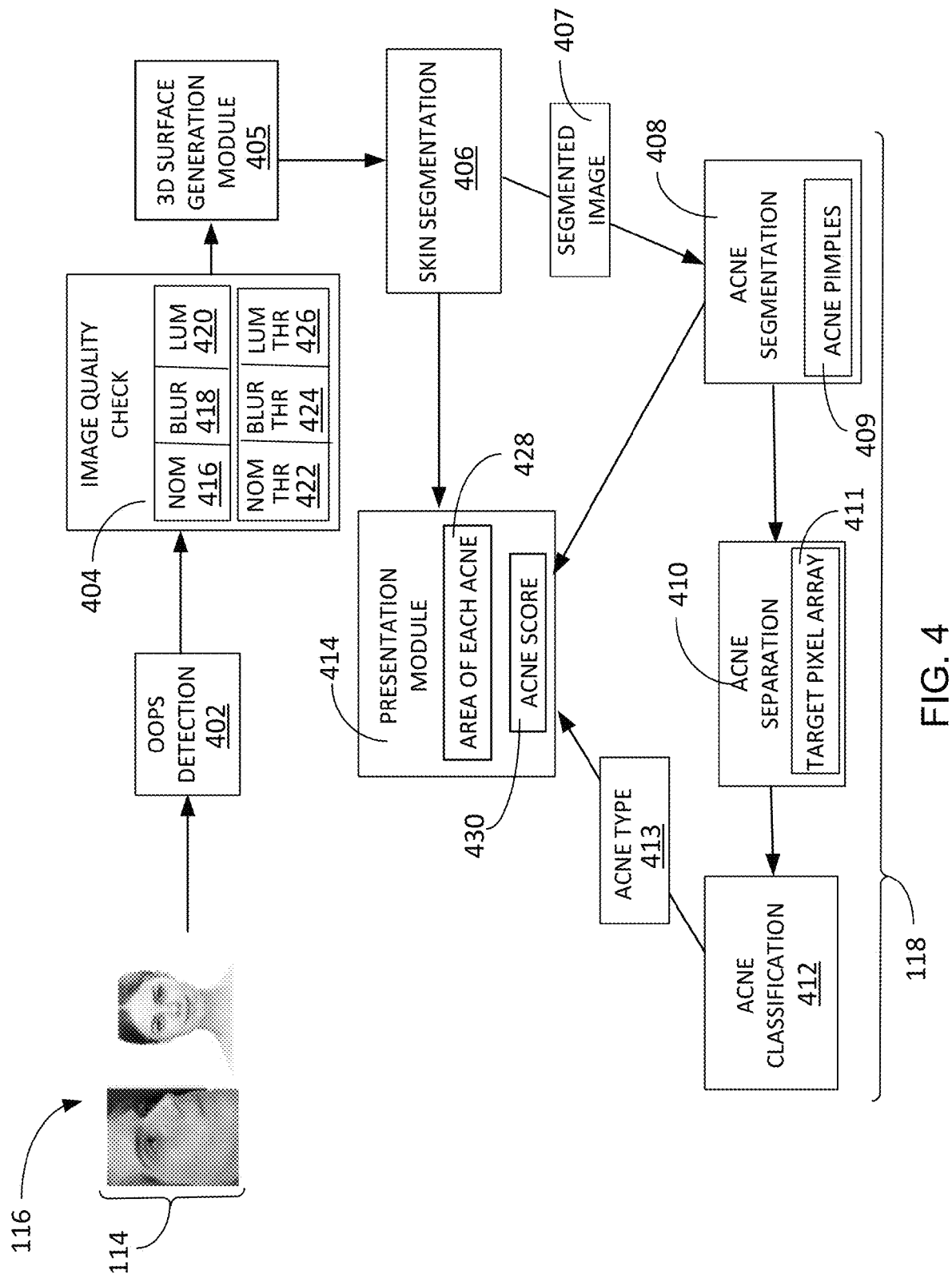
FIG. 4 is an example of a control flow of the compute system with the 3D skin diagnostic mechanism in an embodiment.

Referring now to FIG. 4, therein is shown an example of a block diagram of the compute system 100 with the 3D skin diagnostic mechanism 116 in an embodiment. In the example depicted in FIG. 4, the processing of the input image 114 can be depicted at least as shown in FIG. 2 with acne segmentation 202 and acne classification 204 and can be performed by the compute system 100 of FIG. 1, the 3D skin diagnostic module 116 of FIG. 1, or a combination thereof.

In this example, the input image 114 is processed with Oops detection module 402 to detect whether if the input image 114 is skin related or not. If yes, the flow can continue to Image quality check module 404 to verify if the quality of the input image 114 is sufficiently detailed for detection with the 3D skin diagnostic module 116 utilizing the Skin AI 118 of FIG. 1.

In this example, the block diagram can couple the oops detection module 402 to the image quality check module 404. Continuing the example, the image quality check module 404 can function as a filter for preventing poor quality images from being used as input for an acne classification module 412. Poor quality images refer to images that are too blurry or images that are of too bad luminosity (either too bright, too dark or too noisy). Eventually, the image quality check module 404 is a classification module whose possible output classes are acceptable, blurry, bad luminosity, or a combination thereof for grading the input images 114.

The image quality check module 404 can check the input images 114 for a 3D surface generation module 405 for processing. The 3D surface generation module 405 can be a hardware structure supported by software that can receive the left side image 202 of FIG. 2, the central image 204 of FIG. 2, and the right side image 206 of FIG. 2 for processing a 3D image sequence 208 of FIG. 2. The 3D surface generation module 405 can also process the heat maps 302 of FIG. 3 to enhance the identification of the skin condition under analysis. The generation of the 3D image sequence 208 of FIG. 2 and the 3D heat map sequence 310 of FIG. 3, can improve the processing of the input images 114 by clearly identifying the skin area being processed.

The 3D surface generation module 405 can provide the 3D image sequence 208 and the 3D heat map sequence 310 to a skin segmentation module 406 including a skin module 406, a skin detection module 406, or a combination thereof for processing through the 3D skin diagnostic mechanism 116. The image quality check module 404 can be implemented in a number of ways.

For example, the image quality check module 404 can check the input images 114 that are input for certain quality criteria and meeting or exceeding the quality threshold 122. As specific examples, the quality criteria can include a nominal metric 416, a blurry metric 418, a bad luminosity metric 420, or a combination thereof. Further as a specific example, the quality criteria is a three dimensional vector with the nominal metric 416, the blurry metric 418, and the bad luminosity metric 420.

The nominal metric 416 is used to measure the acceptability of the input images 114 beyond the acceptability by the skin segmentation module 406. The skin segmentation module 406 rejects or accepts each of the input images 114 to include sufficient skin area or skin region as described earlier. The nominal metric 416 processes the input images 114 further such that the image is of sufficient quality to determine a skin diagnosis. The nominal metric 416 represents an overall measure that can be used to determine the acceptability of the input image 114 for skin diagnosis for further processing. The nominal metric 416 can include measures for clarity, lighting, non-intervening obstructions to the visibility of skin, resolution, or a combination thereof.

The blurry metric 418 is used to measure the how clear or blurry the input image 114 being processed is. The value for the blurry metric 418 is set for the input image 114 used for training the image quality check module 404 of what is considered clear and what is consider not clear or blurry. If the value of the blurry metric 418 indicates that the input image 114 is not clear or blurry, then the 3D skin diagnostic mechanism 116 or portions thereof cannot analyze the instance of the input images 114 to compute the acne indication 120. If the value of the blurry metric 418 indicates that the image is clear or not blurry, then the 3D skin diagnostic mechanism 116 or portions thereof can analyze the instance of the input images 114 to compute the acne indication 120.

The bad luminosity metric 420 is used to measure the lighting or brightness or dimness of the input image 114 being processed. The value for bad luminosity metric 420 is set for the input image 114 used for training the image quality check module 404 of what is considered too dim and what is consider not dim. If the value of the bad luminosity metric 420 indicates that the image is dim, then the 3D skin diagnostic mechanism 116 or portions thereof cannot analyze the instance of the 3D image sequence 208 to compute the acne indication 120. If the value of the bad luminosity metric 420 indicates that the image is not too dim, then the 3D skin diagnostic mechanism 116 or portions thereof can analyze the instance of the 3D image sequence 208 to compute the acne indication 120.

The metrics of the quality criteria can be measured with quality threshold 122 collectively, as subsets, as equal priority, or of non-equal priority. The term equal priority refers to all the metrics are compared with equal weight and impact the meeting or exceeding the quality threshold 122 for the 3D image sequence 208 to be deemed acceptable and continue to be processed by the 3D skin diagnostic mechanism 116. The term non-equal priority refers to the varying weight of the metrics relative to each other where some can have more importance over the other metrics. As an example, one of the metrics of the quality criteria alone can be used to determine if the quality threshold 122 is met or not for the image to continue to be processed by the 3D skin diagnostic mechanism 116.

Returning to the quality threshold 122, the quality threshold 122 can include a single value for all or some of the metrics of the quality criteria or can include a value for each of the metrics of the quality criteria. As an example, the quality threshold can include a nominal threshold 422, a blurry threshold 424, a bad luminosity threshold 426, or a combination thereof can be calculated across the 3D image sequence 208 of FIG. 2.

As a specific example, if an instance of the input images 114 is relevant or usable to compute the acne indication 120 by the 3D skin diagnostic mechanism 116, then the skin segmentation module 406 can determine that instance of the 3D image sequence 208 continues processing to the skin segmentation module 406. In this example, the image quality check module 404 checks each of the instance of the input images 114 and outputs a three dimensional vector for the scores for the nominal metric 416, the blurry metric 418, and the bad luminosity metric 420. The value for the bad luminosity metric 420 can also represent the noise in the input image 114 being processed.

Continuing with the specific example, the sum of output vector for the quality criteria does not need to be 1. There can be two high values at the same time: [0.0, 99.6, 98.0] for the nominal metric 416, the blurry metric 418, and the bad luminosity 420, respectively, which means the input image can be blurry or not clear and in bad light quality.

The compute system 100 can set the nominal threshold 422 for the nominal metric 416 for example, if the value for the nominal metric 416 is greater than or equal to 0.6, the image quality check module 404, the 3D skin diagnostic mechanism 116, or a combination thereof accept the input image or the instance of the input images 114 onto the 3D surface generation module 405 being processed at the time. In other words, the nominal metric greater than or equal to the nominal threshold 422 alone can be the quality criteria and serve as the quality threshold, respectively, to determine the input images 114 being processes as acceptable by the image quality check module 404. In this example, the quality criteria can function as a priority encoder with the nominal metric 416 greater than or equal to the nominal threshold 422 to determine acceptability regardless of the values and comparison to the other two metrics and two thresholds.

When the nominal metric 416 is less than the nominal threshold 422, the blurry metric 418 and the bad luminosity metric 429 are compared to the blurry threshold 424 and the bad luminosity threshold 426, respectively. The greater or the maximum value between the blurry metric 418 and the bad luminosity metric 420 will determine whether the blurry threshold 424 or the bad luminosity threshold 426, respectively, shall be used as the quality threshold.

In other words, as an example, if the value of the nominal metric 416 is lower than 0.6 but values for the blurry metric 418 and the bad luminosity metric 420 indicates bad light condition are lower than the blurry threshold 424 and the bad luminosity threshold 426, respectively, then the image quality check module 404, accepts the input image or the instance of the input images 114 being processed at the time. Otherwise, the input image or the instance of the input images 114 being processed at the time will be classified into blurry if the value for the blurry metric 418 is higher than the value for the bad luminosity metric 420 and vice versa. Continuing this example, the quality threshold 122 is shown to be 0.7. Further, the metric (blurry metric 418 or the bad luminosity metric 420) with the larger value can be used to provide feedback to improve performance of the compute system 100 if the image quality check module 404 rejects the image. It is understood that the rejection of the input image 114 by the image quality check module 404 can result in a message to the user 112 of FIG. 1 to retake the input image 114.

Continuing the example, the input images 114 that are processed and determined by the image quality check module 404 to continue processing by the compute system 100, the 3D skin diagnostic module 116, or a combination thereof, the flow can process from the image quality check module 404 to the 3D surface generation module 405 to assemble the left side image 202, the central image 204, and the right side image 206 and convert them to the 3D image sequence 208. The 3D surface generation module 405 can pass the 3D image sequence 208 to the skin segmentation module 406 for further processing.

The skin segmentation module 406 can segment skin region included eyes, nails, tattoo on skin, sick skin (for example psoriasis, skin tumors, etc.). The skin segmentation does not optionally segment scalp unless the scalp is visible (i.e., there are not too much hair covering it). The skin segmentation module 406 can ignore the object on skin such as clothes, bracelet, etc. However, the skin segmentation module 406 can still segment the visible skin like skin under transparent objects, such as glasses.

Continuing with the example, the compute system 100, the 3D skin diagnostic module 116, or a combination thereof can detect skin and blackout all non-skin region of the input image 114 with the skin segmentation module 406. The flow can continue to an acne segmentation module 408 to segment the acne and acne-like area of the segmented image 407. As shown in FIG. 2, the input image 114 is analyzed in small pixel regions to derive the segmented image 202 of FIG. 2. Based on the result of the acne segmentation module 408, the compute system 100, the 3D skin diagnostic module 116, or a combination thereof can continue to Acne separation algorithm (Algorithm A) 410, described later, to get the center and radius information of each of an acne pimples 409 and acne-like areas. The compute system 100, the 3D skin diagnostic module 116, or a combination thereof can crop the segmented image 407 into a target pixel array 411 with one of the acne pimples 409 or acne-like area in the center. The acne separation algorithm 410 can analyze the target pixel array 411 to separate a plurality of the acne pimples 409 that are adjacent in the segmented image 407.

The compute system 100, the 3D skin diagnostic module 116, or a combination thereof can score the cropped images using Acne classification module 412. The skin AI 118 can include the acne segmentation module 408, the acne separation algorithm 410, and the acne classification module 412 for identifying and classifying the acne pimples 409. The Acne classification module 412 can identify each of the acne pimples 409 into acne types 413. The acne types 413 can be identified from among a white head 409, a black head 409, a pustule 409, a cyst 409, a nodule 409, a papule 409, a comedone 409, and a discoloration 409. The Acne classification module 412 generates a score from 0 to 5 for each cropped image. The higher score, the more severe it is. Using the Skin segmentation module 406, Acne segmentation module 408, and the Acne classification 412, the compute system 100, the 3D skin diagnostic module 116, or a combination thereof can compute (Algorithm B) in a presentation module 414 to generate the final score for each of the acne pimples 409 and acne-like area as well as their area.

The compute system 100, the 3D skin diagnostic module 116, or a combination thereof can be trained each module individually. Once every single module performs well (that is the obtained metrics are greater or higher than some good threshold depending on each module. For example, the skin segmentation has to have a similarity coefficient, such as a Jaccard score, higher than 0.8), the compute system 100, the 3D skin diagnostic module 116, or a combination thereof can be trained, tested, or a combination thereof as the whole system together. In this training process, a test set is not part of the training set. The test set can include a variety of data for example different skin tone, different parts of the face or body, different resolution, etc. Every time, if any portion of the compute system 100, the 3D skin diagnostic module 116, or a combination thereof can provide an update, which can be from one module, from one algorithm, the compute system 100, the 3D skin diagnostic module 116, or a combination thereof can predict acne on those images by running through the 3D skin diagnostic mechanism 116. After the raw results, the compute system 100, the 3D skin diagnostic module 116, or a combination thereof can run statistical tests and compare the analysis result with the one of an older version. If the result is better, the compute system 100, the 3D skin diagnostic module 116, or a combination thereof can keep the update. Otherwise, we will not use it.

The compute system 100, the 3D skin diagnostic module 116, or a combination thereof can compute acne severity score as follows:

$$S = \frac{200}{\pi} \arctan\left(c \sum_{i=0}^{N} s_i \frac{a_i}{A}\right) \quad (1.1)$$

where N is total number of acne, c is a fixed coefficient, $s_i$ is the score of acne i, $a_i$ is the area of acne i and A is the total area of detected skin. The arctan function provides a linear increasing for the normal coverage of acne and a quite constant for the very severe acne face see FIG. 5. The acne severity score 430 has minimum value is 0 and maximum value is 100. The skin segmentation is described more later and to compute total skin area and the computation of acne area (described later).

Regarding the performance of the compute system 100, the 3D skin diagnostic module 116, or a combination thereof, a number of metrics can be utilized. There are a number of possible metrics for loss functions and accuracy.

Regarding mean squared error and mean absolute error, if a vector of n predictions is generated from a sample of n data points on all variables, and Y is the vector of observed values of the variable being predicted, with $\hat{Y}$ being the predicted values, then the within-sample Mean squared error (MSE) of the predictor is computed as:

$$MSE = \frac{1}{n}\sum_{i=1}^{n}(Y_i - \hat{Y}_i)^2 \quad (2.1)$$

And the Mean absolute error (MAE) is computed as $$MAE = \frac{1}{n}\sum_{i=1}^{n}|Y_i - \hat{Y}_i| \quad (2.2)$$

These functions can quantify the errors made by the module: the lower their value is, the better it is for the module. They can also be considered as distances between true and predicted values, L1-distance for the MAE, and L2-distance for the MSE. They are mostly used in regression problems, where the output is a real number.

One benefit of the MSE is that it can be optimized due to its derivative. This means that the compute system 100, the 3D skin diagnostic module 116, or a combination thereof can utilize this function as a loss function during the training of a regression problem. On the other side, MAE, which has not this easy optimization property due to the absolute value in its definition, is useful for measuring how far from the true values are predicted values. Indeed, this function gives values in the same scale and unit as the predicted values, which allow more interpretation and understanding for human eyes. Then MAE is often used as a metric during training, to ensure that the module performs well.

Regarding Binary Cross-Entropy loss, binary classification is basically a supervised learning algorithm which aims to classify inputs into one of two classes. The format of the output can be the probability to belong to each class, or directly the predicted class. Useful for binary classification problems with probabilities as output, the Binary Cross-Entropy loss (BCE) is defined as:

$$BCE = -\frac{1}{n}\sum_{i=1}^{n}\left(Y_i \times \log(\hat{Y}_i) + (1 - Y_i) \times \log(1 - \hat{Y}_i)\right) \quad (2.3)$$

This function allows to compare each predicted probabilities $\hat{Y}_i$ to actual class output $Y_i$ which can be either 0 or 1. Then, it calculates the score that penalizes the probabilities based on the distance from the expected value. That means how close or far from the actual value. The BCE is also called the log loss because we apply the logarithm function. The reason behind using the logarithm function is that it penalizes less for small differences between predicted probabilities and true labels, but penalizes more when the difference is larger. Eventually, since the probabilities are between 0 and 1, the log values are negative, that is why the compute system 100, the 3D skin diagnostic module 116, or a combination thereof can take the opposite of the average over the samples, to get a positive BCE value.

Regarding Jaccard score, the Jaccard index, also known as the Jaccard similarity coefficient, is a statistic used for gauging the similarity and diversity of sample sets. It measures the similarity between finite sample sets, it is defined as the ratio of the intersection over the union of the two sets.

$$J(A, B) = \frac{|A \cap B|}{|A \cup B|} \quad (2.4)$$

Regarding intra-class correlation coefficient (ICC), the intra-class correlation coefficient (ICC) is a number, usually found to have a value between 0 and 1. It refers to correlations within a class of data (for example correlations within repeated measurements of weight), rather than to correlations between two different classes of data (for example the correlation between weight and length). Let the variable of observation is defined as:

$$X_{ij} = \mu + \alpha_i + e_{ij} \quad (2.5)$$

Where a is the group effects and e is the residual effects which are independently normally distributed with mean 0 and $$E(X_{ij}) = \mu \text{ and } \text{Var}(\alpha_i) = \sigma_\alpha^2; \text{Var}(e_{ij}) = \sigma_e^2 \quad (2.6)$$

Then the ICC is defined as $$ICC = \frac{\sigma_a^2}{\sigma_a^2 + \sigma_e^2} \quad (2.7)$$

The binary accuracy is defined as the ratio between number of correct predictions over the total number of predictions. For example, let the ground truth is [1, 1, 0, 1, 0, 0] and the prediction is [0, 1, 1, 0, 1, 0], then the number of correct predictions is 2 (the second position and the last position) and the total number of predictions is 6. So, the Binary accuracy in this case is 2/6=1/3. When the compute system 100, the 3D skin diagnostic module 116, or a combination thereof compute Binary accuracy for one image, each pixel of that image is considered as an information valued either 0 or 1. The compute system 100, the 3D skin diagnostic module 116, or a combination thereof can compare the predicted values with the ground truth pixel by pixel and get the Binary accuracy as the above formula.

For example, let the ground truth segmented image 407 (3×5 pixels) A and the prediction B be $$A = \begin{bmatrix} 1 & 0 & 0 & 0 & 0 \\ 0 & 0 & 0 & 0 & 0 \\ 0 & 0 & 0 & 0 & 0 \end{bmatrix}; \text{ and } B = \begin{bmatrix} 0 & 1 & 0 & 0 & 0 \\ 0 & 0 & 0 & 0 & 0 \\ 0 & 0 & 0 & 0 & 0 \end{bmatrix} \quad (2.8)$$

Binary accuracy of this example is 0.8 (there are 12 corrected prediction pixels over 15 pixels). However, Jaccard index in this case is 0 since there is only one annotated pixel which is not matched by the prediction.

The Oops detection module 402 can acts as a filter, preventing irrelevant images to be used as input for the image quality check module 404. An irrelevant image refers to images that do not contain human skin or has more than 80% background. Eventually, the Oops detection module 402 is a regression module whose output gets a value between 0 and 1 in which a value close to 1 means probably irrelevant and vice versa. The compute system 100, the 3D skin diagnostic module 116, or a combination thereof can include a threshold equal to 0.8 to separate the region of irrelevant and relevant, i.e., if output is greater than 0.8, the input is irrelevant, otherwise it is relevant.

As an example, the ImageNet dataset contains 310K images in which there are 34K irrelevant images and the remaining are relevant images. The dataset includes a variety of images of animals, plants, foods and people. It also includes images with very sick skin to normal skin in wide range of skin tone from white to darker skin.

The Oops detection module 402 not only filters irrelevant images, but also to eliminate an image taken from too far distance which makes the human skin part cover less than 20% area. To be able to detect the case, the compute system 100 includes a set of data in which there are images containing human skin covering less than 20% area. The dataset is supplemented with data augmentation creating a set of 94K synthetic images in which a relevant image is merged with an irrelevant one to get a synthetic image in which the background of the relevant image is expanded.

The skin segmentation module 406 can be implemented in a number of ways. As an example, the implementation can be U-net architecture, which includes of an encoder-decoder scheme. The encoder reduces the spatial dimensions in every layer and increases the channels. The decoder increases the spatial dims while reducing the channels. As a specific example, EfficientNet architecture, which is a convolutional neural network architecture and scaling method that uniformly scales all dimensions of depth/width/resolution using a compound coefficient, can be an implementation for the classification and pre-trained on ImageNet dataset for the encoding.

Continuing with the example, the process can continue from the skin segmentation module 406 to the acne segmentation module 408. As an example, the acne segmentation module 408 does not just segment the acne but it also segments the acne-like marks, for example acne scar or mole. The acne segmentation module 408 performs an object detection where compute system 100, the 3D skin diagnostic module 116, or a combination thereof can detect every acne pimple 409, such as irritated regions of the skin at or near the surface even of very small size. These are challenging problems because machine can get high accuracy without detecting anything. For example, if there are only 5% of skin area having acne, the machine will get 95% accuracy when it detects no acne and the acne pimples 409 do not often have well-defined borders which makes the acne segmentation task even more difficult. As a result, different doctors may segment the acne pimples 409 differently. Therefore, it is very hard to make the machine learn the correct acne segmentation. The compute system 100, the 3D skin diagnostic module 116, or a combination thereof addresses these challenging problems at least through the selection of the architecture and training dataset.

Continuing with the example, the process can continue from the acne segmentation module 408 to the acne classification module 412, the acne separation module 410, or a combination thereof.

The acne classification module 412 can be trained in a number of ways with various datasets. For example, the acne classification module 412 can be trained with 128×128 pixels images. The training images are cut based on the acne segmentation module 408. That is, after detecting the acne spots, the acne classification module 412 identifies the center point of each acne and let it be the center of 128×128 pixels image. In the input image, there can be many acne pimples 409. The acne classification module 412 focuses on the acne at the center of the image and classify it, but do not classify the ones not in the center. For example, the acne classification module 412 utilizes region of interest (ROI) technique to focus on the chosen acne in the input image 114. That is the inputs of acne classification module 412 are one RGB image and one ROI image. As a specific example, the acne classification module can be based on an Xception structure, which is a deep convolutional neural network architecture, with a residual layer and multiplication step between original image and ROI.

In the example shown in FIG. 4, the acne separation module 410 is shown between the acne segmentation module 408 and the acne classification module 412, although the compute system 100, the 3D skin diagnostic module 116, or a combination thereof can be implemented differently. For example, the acne separation module 410 can be implemented as part of the acne segmentation module 408 and the acne classification module 412, or distributed between two.

The acne separation module 410 improves the performance of the acne classification module 412 because the acne segmentation module 408 can output the acne pimples 409 that is right next to another of the acne pimples 409 as one. The erroneous segmentation input to the acne classification module 412 results in an incorrect classification either because the two of the acne pimples 409 are of different types or the acne classification module 412 will see two of the acne pimples 409 as one hence the area or the size will be bigger. All of this sequence can produce an incorrect prediction. The acne separation module 410 can separate the acne pimples 409 that are right next to another of the acne pimples 409 by dividing the image into a target pixel array 411 each containing a single instance of the acne pimples 409. The target pixel array 411 can be the smallest pixel array suitable for analysis of the acne pimples 409. By way of an example, the target pixel array 411 can be the 32×32×1024 pixel array 411 for the image quality check module 404, the 12×12×1632 pixel array 411 for the skin segmentation module 406, and the 16×16×1632 pixel array 411 for the acne segmentation module 408.

The flow can progress with one or more of the following leading to the presentation module 414. As an example, the presentation module 414 can process inputs from the skin segmentation module 406, the acne segmentation module 408, the acne classification module 412, or a combination thereof. The compute system 100, the 3D skin diagnostic module 116, display module 414, or a combination thereof can return the area of each type of acne as well as the area of each acne. To do that, the result from Acne classification module 412. Acne segmentation module 408, and Skin segmentation module 406 can be overlayed to form the acne indication 120.

By way of an example, the Skin segmentation module 406 can provide the segmented image 407, the Acne segmentation module 408 can provide the region of interest (ROI) having evidence of acne in the segmented image 407, and the Acne classification module 412 can provide an area of each acne 428 and an acne severity score 430. The compilation of the outputs of the Acne classification module 412, Acne segmentation module 408, and Skin segmentation module 406 can form the acne indication 120 including the 3D image sequence 208.

The functional units or circuits in the first device 102 can work individually and independently of the other functional units or circuits. The first device 102 can work individually and independently from the network 104, the second device 106, other devices or vehicles, or a combination thereof.

The functional units or circuits described above can be implemented in hardware. For example, one or more of the functional units or circuits can be implemented using a gate, circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

Figure 5:
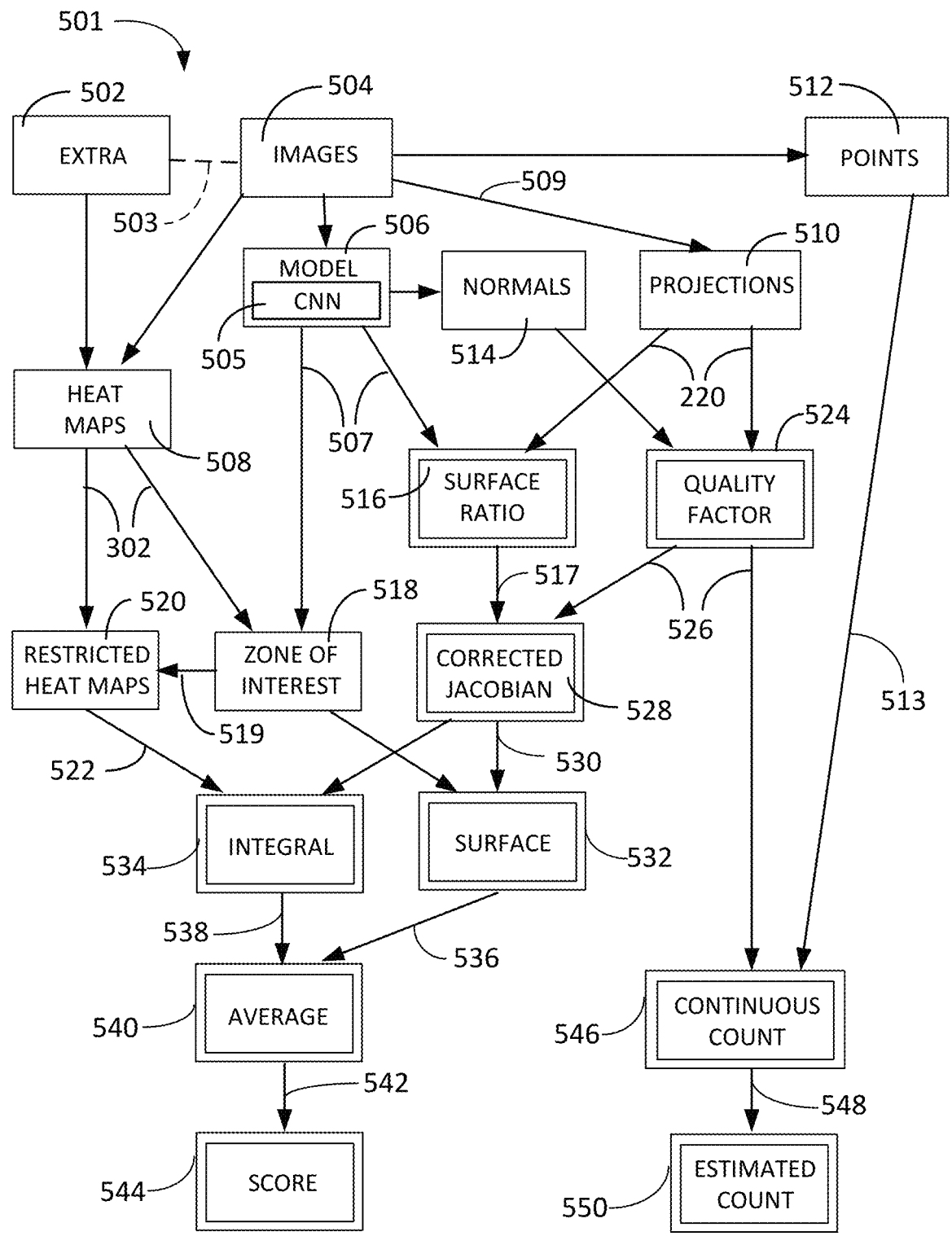
FIG. 5 is an example of a functional block diagram of the 3D skin diagnostic module in an embodiment of the present invention.

Referring now to FIG. 5, therein is shown an example of a functional block diagram 501 of the 3D skin diagnostic module 116 in an embodiment of the present invention. The functional block diagram of the 3D skin diagnostic module 116 depicts an extra module 502 linked to an images module 504. The images module 504 can be a hardware structure managed by software to receive the input images 114 of FIG. 1. Each of the input image 114 can include metadata 503 defining the instance of the input image 114. The extra module 502 can receive the metadata for the input image 114. The metadata can include the focal length of the input image 114, the date, time, location, optical, infrared, or a combination thereof can be included.

The images module 504 can pass pixels 509 of the input image 114 to a model module 506, a heat maps module 508, a projections module 510, and a points module 512. The model module 506 can be a hardware structure managed by software to receive the pixels 509 of the input images 114. The model module 506 can compute a three-dimensional model of the input images 114. By way of an example the model module 506 can include a convolutional neural network 505 trained with MediaPipe's Face Mesh library to compute a digital model 507 from the pixels 509 of the input image 114 by applying the triangular mesh 216 of FIG. 2 on a zone of interest 519. The zone of interest 519 can be a selected one of the 3D-polygons 220 of FIG. 2 segmenting the pixels 509 being analyzed.

The heat maps module 508 can be a hardware structure managed by software to receive the left side heat map 304 of FIG. 3, the central heat map 306 of FIG. 3, and the right side heat map 308 of FIG. 3 in order to generate the 3D heat map sequence 310 of FIG. 3. For each of the input image 114, a corresponding heat map 302 related to the function we want to measure can be computed. For example, the skin AI 118 of FIG. 1 can estimate the severity of the lesions on the input image 114, i.e. the value of the heatmap is high if the corresponding ones of the pixels 509 on the input image 114 corresponds to a severe lesion, if the value is low then the lesion is not severe, and the value is zero if there is no lesion.

The projections module 510 can be a hardware structure managed by software configured to examine the input image 114 to identify a projection point which maps a point of the 3D-model to the input image 114. Here, as the model is approximated by 3D-polygons, the projection can be simply approximated by knowing the corresponding position of each vertex on the image. The full projection of points 512 in the input image 114 can be deduced by linear interpolation.

The points module 512 can be an indication of the skin condition segmented from the input image 114 as identified points 513. A list of the identified points 513 on each of the input image 114, with potential errors. For example, in an independent process the identified points 513 can be identified as acne, and the computational model might miss some or find some extra false one.

The model module 506 can be coupled to a normals module 514, a surface ratio module 516, and a zone of interest module 518. The normals module 514 can be a hardware structure managed by software configured to identify typical values at each vertex of the digital model. The normal at a vertex is the average of all normals of faces incident to this vertex. The normal at an arbitrary point in a surface is the weighted average of normal at vertex incident to the face depicted in the input image 114.

The surface ratio module 516 is a hardware structure managed by software that is configured to compute the heat map 302 indicating the 'density', i.e. how much surface on the object does one pixel of the image represent (0) if it is outside). For this computation, the heat map 302 is initialized to 0, then for each triangle of the 3D-model 517, its projection on the image is computed, and draw the triangle on the heat map 302 filled with value being the ratio of the surface of triangle of the model and the surface of the triangle on the image. If a large triangle of the 3D-model 517 is projected to a small triangle on the input image 114, the corresponding ones of the pixels 509 on the surface ratio heatmap is large, on the other hand, if a small triangle of the model is projected to a large triangle of the image, the surface ratio heatmap here is small.

The zone of interest module 518 can be a hardware structure managed by software that is configured to restrict our estimation to a smaller part of the model, or anything wanted the "Zone of interest" are binary (or gray-scale) heatmaps, which describe for each of the pixels 509 of the image whether or not it counts. It should be binary, however if there is any measurement error or uncertainty, a continuous value in [0, 1] is allowed describing the probability/proportion of the pixels 509 being in a zone of interest 519.

The zone of interest module 518 can be coupled to the heat maps module 508 to receive the heat maps 302 that are applied to the digital model 507 provided by the model module 506. The heat map 302 can indicate areas in the digital model 507 that require further analysis. The zone of interest module 518 can output the zone of interest 519 to a restricted heat maps module 520).

The restricted heat maps module 520 can apply the zone of interest 519 to the heat maps 302 in order to generate the restricted heat map 522. Each of the heat maps 302 is multiplied by the zone of interest 519, in order to obtain the restricted heat maps 522, which have 0 values outside the zone of interest 519. This ensures that anything outside the zone of interest 519 have no influence on the final result.

The projections module 510 can segment the 3D-polygons 220 that represent each vertex identified in the input image 114 by applying the triangular mesh 216. The projections module 510 can be coupled to the surface ratio module 516 and a quality factor module 524.

The surface ratio module 516 can use the 3D-polygons 220 of the pixels 509 of the input image 114 as applied to the digital model 507.

The quality factor module 524 can be a hardware structure managed by software configured to compute the heat map 302 indicating how trustworthy are the corresponding pixels 509 of the input image 114, in relation to heat maps 302. By way of an example, the idea that it is easier to interpret (part of) an image, is the direction of the camera is orthogonal to the surface of the object, equivalently if the direction of the camera is the same as normal to the surface of the object.

A quality factor 526 is first (virtually) computed on the digital model 507, then projected on the heat map 302. The quality factor 526 at a point of the model, for the input image 114, is proportional to (a power of) the scalar product of the normal at this point and the direction of the camera and 0 if it is negative or if the point is not visible on the projection. The sum of the quality factor 526, at a point, for all of the input image 114 is always 1 (unless the model's point is not visible on the input image 114, in this case it is 0). The quality factor module 524 can project the quality factors 526 on the corresponding versions of the heat maps 302.

The quality factor module 524 can provide the quality factor 526 to a corrected Jacobian module 528. The corrected Jacobian module 528 also receives input of the 3D-model 517 from the surface ration module 516. The corrected Jacobian module 528 can be a hardware structure managed by software that is configured to compute the point-wise product of the heat maps 302 of the quality factor 526 and the 3D-model 517 to produce a correlated model 530.

The corrected Jacobian module 528 can provide the correlated model 530 to a surface module 532 and an integral module 534. The surface module 532 can be a hardware structure managed by software that is configured to compute the scalar product of each of the zone of interest 519 with the corresponding sections of the correlated model 530. By way of an example, the sum of all obtained scalars is a 3D surface 536 assembled by compiling the zone of interest 519 for each of the 3D-polygons 220. It is understood that the compiling of the zone of interest 519 for each of the 3D-polygons 220 is performed by pixel matching the 3D-polygons 220 containing the pixels 509 from the left side image 202 of FIG. 2, the central image 204 of FIG. 2, the right side image 206 of FIG. 2, or a combination thereof to match the digital model 507.

The integral module 534 can be a hardware structure managed by software that is configured to compute the scalar product of the restricted heat map 522 and the correlated model 530. The integral module 534 can compute the sum of all of the restricted heat map 522 and the correlated model 530. The integral module 534 provides a severity profile 538 of the function, such as the detection of the condition 218 of FIG. 2, measured by the heat maps 302 over the zone of interest 519.

An average module 540 can be a hardware structure managed by software that is configured to compute the quotient of the integral over the 3D surface 536, it gives an average threshold value 542 of the function, such as the value of the pixels 509, over the zone of interest 519. A score module 544 can compile the acne severity score 430 of FIG. 4 for the 3D surface 536. The score module 544 can be a hardware structure managed by software that is configured to compute the compile the acne severity score 430 for the 3D surface 536 for providing a single reference threshold across the 3D surface 536.

The quality factor module 524 can provide the quality factor 526 to a continuous count module 546. The continuous count module 546 can be a hardware structure managed by software that is configured to compute a total item count 548 of the identified points 513, by taking the sum of all values for the quality factor 526 on coordinates of the identified points 513, weighted by the probability, if relevant. The continuous count module 546 can provide a continuous estimate of the total number of the identified points 513. An estimated count module 550 can be a hardware structure managed by software that is configured to keep a running total of the identified points 513.

While the functional block diagram 501 has been described in the analysis of the input image 114 to identify the acne severity score 430, it is understood that the structure can be used to identify other functions that can be identified in input images. It is possible to estimate several functions, corresponding to several of the heat maps 302 for each input images, without having to redo all computations. The functional block diagram 501 compute the heat maps 302, zone of interest 519, the restricted heat maps 522, the severity profile 538, the average threshold value 542, and the acne severity score 430 for each additional function. In current application the restricted heat maps 522 is restricted to the zone of interest 519, however it is not required, both could even be disjoint.

Figure 6:
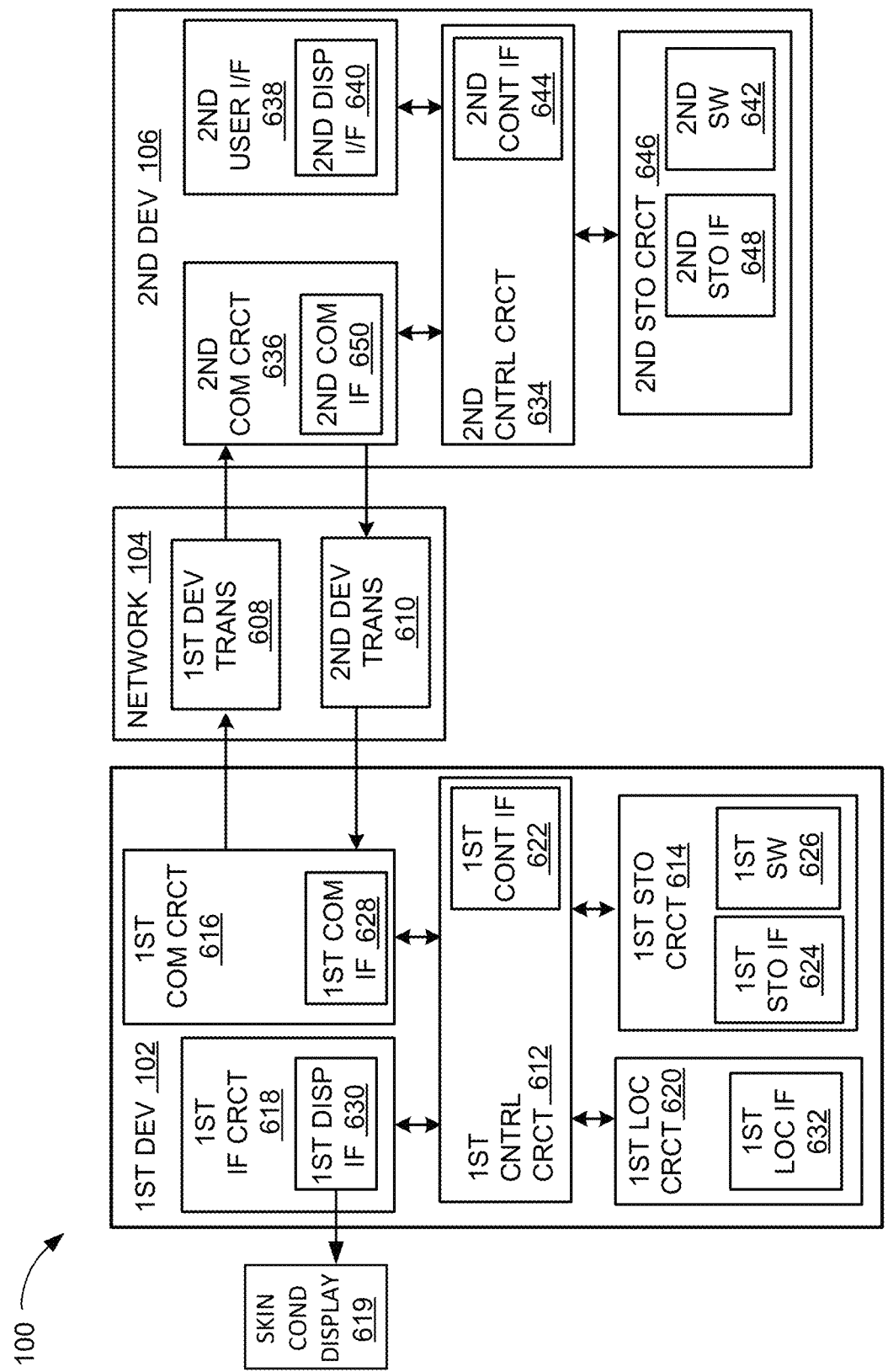
FIG. 6 is an exemplary block diagram of the compute system in an embodiment.

Referring now to FIG. 6, therein is shown an exemplary block diagram of the compute system 100 in an embodiment. The compute system 100 can include the first device 102, the network 104, and the second device 106. The first device 102 can send information in a first device transmission 608 over the network 104 to the second device 106. The second device 106 can send information in a second device transmission 610 over the network 104 to the first device 102 or the vehicle 201 of FIG. 2.

For illustrative purposes, the compute system 100 is shown with the first device 102 as a client device, although it is understood that the compute system 100 can include the first device 102 as a different type of device.

Also, for illustrative purposes, the compute system 100 is shown with the second device 106 as a server, although it is understood that the compute system 100 can include the second device 106 as a different type of device. For example, the second device 106 can be a client device. By way of an example, the compute system 100 can be implemented entirely on the first device 102.

Also, for illustrative purposes, the compute system 100 is shown with interaction between the first device 102 and the second device 106. However, it is understood that the first device 102 can be a part of or the entirety of an autonomous vehicle, a smart vehicle, or a combination thereof. Similarly, the second device 106 can similarly interact with the first device 102 representing the autonomous vehicle, the intelligent vehicle, or a combination thereof.

For brevity of description in this embodiment of the present invention, the first device 102 will be described as a client device and the second device 106 will be described as a server device. The embodiment of the present invention is not limited to this selection for the type of devices. The selection is an example of an embodiment of the present invention.

The first device 102 can include a first control circuit 612, a first storage circuit 614, a first communication circuit 616, a first interface circuit 618, and a first location circuit 620. The first control circuit 612 can include a first control interface 622. The first control circuit 612 can execute a first software 626 to provide the intelligence of the compute system 100.

The first control circuit 612 can be implemented in a number of different manners. For example, the first control circuit 612 can be a processor, an application specific integrated circuit (ASIC) an embedded processor, a microprocessor, a hardware control logic, a hardware finite state machine (FSM), a digital signal processor (DSP), or a combination thereof. The first control interface 622 can be used for communication between the first control circuit 612 and other functional units or circuits in the first device 102. The first control interface 622 can also be used for communication that is external to the first device 102.

The first control interface 622 can receive information from the other functional units/circuits or from external sources, or can transmit information to the other functional units/circuits or to external destinations. The external sources and the external destinations refer to sources and destinations external to the first device 102.

The first control interface 622 can be implemented in different ways and can include different implementations depending on which functional units/circuits or external units/circuits are being interfaced with the first control interface 622. For example, the first control interface 622 can be implemented with a pressure sensor, an inertial sensor, a microelectromechanical system (MEMS), optical circuitry, waveguides, wireless circuitry, wireline circuitry, or a combination thereof.

The first storage circuit 614 can store the first software 626. The first storage circuit 614 can also store the relevant information, such as data representing incoming images, data representing previously presented image, sound files, or a combination thereof.

The first storage circuit 614 can be a volatile memory, a nonvolatile memory, an internal memory, an external memory, or a combination thereof. For example, the first storage circuit 614 can be a nonvolatile storage such as non-volatile random-access memory (NVRAM), Flash memory, disk storage, or a volatile storage such as static random-access memory (SRAM).

The first storage circuit 614 can include a first storage interface 624. The first storage interface 624 can be used for communication between the first storage circuit 614 and other functional units or circuits in the first device 102. The first storage interface 624 can also be used for communication that is external to the first device 102.

The first storage interface 624 can receive information from the other functional units/circuits or from external sources, or can transmit information to the other functional units/circuits or to external destinations. The external sources and the external destinations refer to sources and destinations external to the first device 102. The first storage interface 624 can receive input from and source data to the 3D skin diagnostic module 116.

The first storage interface 624 can include different implementations depending on which functional units/circuits or external units/circuits are being interfaced with the first storage circuit 614. The first storage interface 624 can be implemented with technologies and techniques similar to the implementation of the first control interface 622.

The first communication circuit 616 can enable external communication to and from the first device 102. For example, the first communication circuit 616 can permit the first device 102 to communicate with the second device 106 and the network 104.

The first communication circuit 616 can also function as a communication hub allowing the first device 102 to function as part of the network 104 and not limited to be an endpoint or terminal circuit to the network 104. The first communication circuit 616 can include active and passive components, such as microelectronics or an antenna, for interaction with the network 104.

The first communication circuit 616 can include a first communication interface 628. The first communication interface 628 can be used for communication between the first communication circuit 616 and other functional units or circuits in the first device 102. The first communication interface 628 can receive information from the second device 106 for distribution to the other functional units/circuits or can transmit information to the other functional units or circuits.

The first communication interface 628 can include different implementations depending on which functional units or circuits are being interfaced with the first communication circuit 616. The first communication interface 628 can be implemented with technologies and techniques similar to the implementation of the first control interface 622.

The first interface circuit 618 allows the user 112 of FIG. 1 to interface and interact with the first device 102. The first interface circuit 618 can include an input device and an output device. Examples of the input device of the first interface circuit 618 can include a keypad, a touchpad, soft-keys, a keyboard, a microphone, an infrared sensor for receiving remote signals, or any combination thereof to provide data and communication inputs.

The first interface circuit 618 can include a first display interface 630. The first display interface 630 can include an output device. The first display interface 630 can include a projector, a video screen, a touch screen, a speaker, a microphone, a keyboard, and combinations thereof.

The first control circuit 612 can operate the first interface circuit 618 to display a skin condition display 619 assembled by the 3D skin diagnostic module 116 of FIG. 1 and receive input from the user 112. The skin condition display 619 can include the the acne score 430 of FIG. 4, the area of each acne 428 of FIG. 4, the estimated count 550) of FIG. 5, and the 3D image sequence 208 of FIG. 2 including the condition 218 of FIG. 2 and the identifying marker 219 of FIG. 2. The first control circuit 612 can also execute the first software 626 for the other functions of the compute system 100, including receiving location information from the first location circuit 620. The first control circuit 612 can further execute the first software 626 for interaction with the network 104 via the first communication circuit 616. The first control circuit 612 can operate the 3D skin diagnostic mechanism 116 of FIG. 1.

The first control circuit 612 can also receive location information from the first location circuit 620. The first control circuit 612 can operate the 3D skin diagnostic module 116.

The first location circuit 620 can be implemented in many ways. For example, the first location circuit 620 can function as at least a part of the global positioning system, an inertial compute system, a cellular-tower location system, a gyroscope, or any combination thereof. Also, for example, the first location circuit 620 can utilize components such as an accelerometer, gyroscope, or global positioning system (GPS) receiver.

The first location circuit 620 can include a first location interface 632. The first location interface 632 can be used for communication between the first location circuit 620 and other functional units or circuits in the first device 102, including the environmental sensors 210.

The first location interface 632 can receive information from the other functional units/circuits or from external sources, or can transmit information to the other functional units/circuits or to external destinations. The external sources and the external destinations refer to sources and destinations external to the first device 102. The first location interface 632 can receive the global positioning location from the global positioning system (not shown).

The first location interface 632 can include different implementations depending on which functional units/circuits or external units/circuits are being interfaced with the first location circuit 620. The first location interface 632 can be implemented with technologies and techniques similar to the implementation of the first control circuit 612.

The second device 106 can be optimized for implementing an embodiment of the present invention in a multiple device embodiment with the first device 102. The second device 106 can provide the additional or higher performance processing power compared to the first device 102. The second device 106 can include a second control circuit 634, a second communication circuit 636, a second user interface 638, and a second storage circuit 646.

The second user interface 638 allows an operator (not shown) to interface and interact with the second device 106. The second user interface 638 can include an input device and an output device. Examples of the input device of the second user interface 638 can include a keypad, a touchpad, soft-keys, a keyboard, a microphone, or any combination thereof to provide data and communication inputs. Examples of the output device of the second user interface 638 can include a second display interface 640. The second display interface 640) can include a display, a projector, a video screen, a speaker, or any combination thereof.

The second control circuit 634 can execute a second software 642 to provide the intelligence of the second device 106 of the compute system 100. The second software 642 can operate in conjunction with the first software 626. The second control circuit 634 can provide additional performance compared to the first control circuit 612.

The second control circuit 634 can operate the second user interface 638 to display information. The second control circuit 634 can also execute the second software 642 for the other functions of the compute system 100, including operating the second communication circuit 636 to communicate with the first device 102 over the network 104.

The second control circuit 634 can be implemented in a number of different manners. For example, the second control circuit 634 can be a processor, an embedded processor, a microprocessor, hardware control logic, a hardware finite state machine (FSM), a digital signal processor (DSP), or a combination thereof.

The second control circuit 634 can include a second control interface 644. The second control interface 644 can be used for communication between the second control circuit 634 and other functional units or circuits in the second device 106. The second control interface 644 can also be used for communication that is external to the second device 106.

The second control interface 644 can receive information from the other functional units/circuits or from external sources, or can transmit information to the other functional units/circuits or to external destinations. The external sources and the external destinations refer to sources and destinations external to the second device 106.

The second control interface 644 can be implemented in different ways and can include different implementations depending on which functional units/circuits or external units/circuits are being interfaced with the second control interface 644. For example, the second control interface 644 can be implemented with a pressure sensor, an inertial sensor, a microelectromechanical system (MEMS), optical circuitry, waveguides, wireless circuitry, wireline circuitry, or a combination thereof.

The second storage circuit 646 can store the second software 642. The second storage circuit 646 can also store the information such as data representing incoming images, data representing previously presented image, sound files, or a combination thereof. The second storage circuit 646 can be sized to provide the additional storage capacity to supplement the first storage circuit 614.

For illustrative purposes, the second storage circuit 646 is shown as a single element, although it is understood that the second storage circuit 646 can be a distribution of storage elements. Also, for illustrative purposes, the compute system 100 is shown with the second storage circuit 646 as a single hierarchy storage system, although it is understood that the compute system 100 can include the second storage circuit 646 in a different configuration. For example, the second storage circuit 646 can be formed with different storage technologies forming a memory hierarchal system including different levels of caching, main memory, rotating media, or off-line storage.

The second storage circuit 646 can be a controller of a volatile memory, a nonvolatile memory, an internal memory, an external memory, or a combination thereof. For example, the second storage circuit 646 can be a controller of a nonvolatile storage such as non-volatile random-access memory (NVRAM), Flash memory, disk storage, or a volatile storage such as static random access memory (SRAM).

The second storage interface 648 can receive information from the other functional units/circuits or from external sources, or can transmit information to the other functional units/circuits or to external destinations. The external sources and the external destinations refer to sources and destinations external to the second device 106.

The second storage interface 648 can include different implementations depending on which functional units/circuits or external units/circuits are being interfaced with the second storage circuit 646. The second storage interface 648 can be implemented with technologies and techniques similar to the implementation of the second control interface 644.

The second communication circuit 636 can enable external communication to and from the second device 106. For example, the second communication circuit 636 can permit the second device 106 to communicate with the first device 102 over the network 104.

The second communication circuit 636 can also function as a communication hub allowing the second device 106 to function as part of the network 104 and not limited to be an endpoint or terminal unit or circuit to the network 104. The second communication circuit 636 can include active and passive components, such as microelectronics or an antenna, for interaction with the network 104.

The second communication circuit 636 can include a second communication interface 650. The second communication interface 650) can be used for communication between the second communication circuit 636 and other functional units or circuits in the second device 106. The second communication interface 650 can receive information from the other functional units/circuits or can transmit information to the other functional units or circuits.

The second communication interface 650 can include different implementations depending on which functional units or circuits are being interfaced with the second communication circuit 636. The second communication interface 650 can be implemented with technologies and techniques similar to the implementation of the second control interface 644.

The second communication circuit 636 can couple with the network 104 to send information to the first device 102. The first device 102 can receive information in the first communication circuit 616 from the second device transmission 610 of the network 104. The compute system 100 can be executed by the first control circuit 612, the second control circuit 634, or a combination thereof. For illustrative purposes, the second device 106 is shown with the partition containing the second user interface 638, the second storage circuit 646, the second control circuit 634, and the second communication circuit 636, although it is understood that the second device 106 can include a different partition. For example, the second software 642 can be partitioned differently such that some or all of its function can be in the second control circuit 634 and the second communication circuit 636. Also, the second device 106 can include other functional units or circuits not shown in FIG. 6 for clarity.

The functional units or circuits in the first device 102 can work individually and independently of the other functional units or circuits. The first device 102 can work individually and independently from the second device 106 and the network 104.

The functional units or circuits in the second device 106 can work individually and independently of the other functional units or circuits. The second device 106 can work individually and independently from the first device 102 and the network 104.

The functional units or circuits described above can be implemented in hardware. For example, one or more of the functional units or circuits can be implemented using a gate array, an application specific integrated circuit (ASIC), circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

For illustrative purposes, the compute system 100 is described by operation of the first device 102 and the second device 106. It is understood that the first device 102 and the second device 106 can operate any of the modules and functions of the compute system 100.

The combination of the first control circuit 612 and the second control circuit 634 can execute the first software 626 and the second software 642 in order to estimate the 3D surface 536 and evaluate the average threshold value 542 of function 536 over the 3D surface 536, given pictures of a 3D-object. The combination of the first control circuit 612 and the second control circuit 634 can provide a continuous computational process, that is if we slightly move or changes the points or functions, the computed value remain stable.

Given a geometric surface Sur of a three-dimensional object, and a function f:Sur→R, in order to compute the average of the function f over Sur, that is:

$$A = \frac{\int_{u \in Sur} f(u) du}{\int_{u \in Sur} 1 du} \quad (6.1)$$

Similarly given a (measurable) subset P of Sur we want to average f over P, that is compute:

$$A = \frac{\int_{u \in P} f(u) du}{\int_{u \in P} 1 du} \quad (6.2)$$

However, the surface Sur, the function f, nor the subset P are given. Instead, one or more pictures of the object, and the function f is estimated on the picture, typically with the Convolutional Neural Network 505 of FIG. 5. The functions that approximate the projections from the 3D-object to the picture. We consider the following objects however, we do not have "computational" access to the following objects.

A surface Sur that can be captured in an image.

The function f: Sur→R.

An integer n>1, and projections $\pi 1, \ldots, \pi n: V \to [0, 1]^2$.

For each i a subset $S_i$ of Sur which should be understood as elements visible on the projection $\pi_i$.

For each i, a normal vector di which is the direction of the projection $\pi_i$.

Some finite set V⊆Sur of key-points.

For each u∈Sur the normal vector $\vec{n}(u)$ to Sur at u.

For each u∈Sur and each 1≤i≤n, consider $$ji(u) = \lim \frac{s(T)}{s(\pi i(T))},$$

the limit taken over the 3D-polygon 220, such as a triangle containing u.

It is assumed that the following are given instead:

A polygonal approximation Sur' of Sur with set of vertices identified with V.

An approximate value of average $\pi i(v) \approx \pi i(v)$ for all 1≤i≤n and all v∈V.

For each i a map fi:[0, 1]²→R, such that fi(πi(u))≈f(u) when u∈$Sur_i$.

We fix a real number q>0.

We consider the function: $\mu_i: Sur_i \to R^+$ $$u \to \max(0, \vec{d}_i \cdot \vec{n}_i(u))^q \quad (6.3)$$

The function $\mu_i$ measure how the normal at some point of Sur is close to the direction $d_i$ of the projection $\pi_i$. We make the following hypothesis:

Every point of the surface Sur is visible on some picture:

$$Sur = Sur_1 \cup Sur_2 \cup \ldots \cup Sur_n. \quad (6.4)$$

Approximations are more precise when the direction of the projection is close to the normal:

$$\int_{u \in Sur_i} |\mu i(u)(fi(\pi i(u)) - f(u))| < \varepsilon i \quad (6.5)$$

We first define continuous function $\lambda 1, \ldots, \lambda n: S \to [0, 1]$ such that:

$\Sigma_i \lambda i(u) = 1$ for all u∈Sur and $\lambda i(u) = 0$ when u not $\in Sur_i$.

$$Set: \lambda i(u) \frac{\mu i(u)}{\sum_{i=1}^{n} \mu i(u)} \quad (6.6)$$

We can compute $\lambda i(x,y)$ such that $\lambda i(\pi i(u)) \approx \lambda i(u)$ We use a classical approximation of normal at a surface considering a polygonal approximation. For each v in V we consider $n_v$ the average of the normals to all face of Sur' incident to v. Then consider for each u in Sur', the (weighted) average of all n, for v incident to the face containing u. We denote by $n_i(x,y)$ this approximate normal vector to Sur at point $\pi_i^{-1}(x,y)$. Let $$\mu i(x,y) = \max(0, \vec{d}_i \cdot ni(x,y))^q \quad (6.7)$$

And $$\lambda_i(x, y) = \frac{\mu i(x, y)}{\sum_{i=1}^{n} \mu i(x, y)} \quad (6.8)$$

Lemma 1. Let ABC and A'B'C' be directed triangles of surfaces respectively Sur and Sur'. Let p: ABC→A'B'C' be the unique affine map such that p(A)=A', p(B)=B', and p(C)=C'. Then we have |det Jp(U)|=Sur'/Sur for all U in the triangle ABC.

Proof. For the sake of simplicity we can assume that C=C' is the origin, and both triangle are in $\mathbb{R}^2$. Denote respectively by $(x_A, y_A)$, $(x_B, y_B)$, $(x'_A, y'_A)$, $(x'_B, y'_B)$ the coordinates of A, B, A', B'. We observe that $S = x_B y_A - x_A y_B$ and $s' = x'_B y'_A - x'_A y'_B$.

As p is linear there are $\alpha 1, \beta 1, \alpha 2, \beta 2$ such that $p(x,y) = (\alpha 1 x + \beta 1 y, \alpha 2 x + \beta 2 y)$ for all $(x,y) \in \mathbb{R}^2$. As $p(x_A, y_A) = (x'_A, y'_A)$ and $p(x_B, y_B) = (x'_B, y'_B)$ we can compute the $\alpha_1, \beta_1, \alpha_2, \beta_2$:

$$\alpha_1 = \frac{x'_A y B - x'_B y A}{x A y B - x B y A} \quad \beta 1 = \frac{x'_A x B - x A x'_B}{x B y A - x A y B}$$

$$\alpha 2 = \frac{y'_A y B - y'_B y A}{x A y B - x B y A} \quad \beta 2 = \frac{y'_A x B - x A y'_B}{x B y A - x A y B}$$

Obtains:

$$|\det J_p(U)| = \begin{vmatrix} \alpha 1 & \beta 1 \\ \alpha 2 & \beta 2 \end{vmatrix}$$

$$= \alpha 1 \beta 2 - \alpha 2 \beta 1$$

$$= \frac{(x'AyB - x'ByA)(y'AxB - xAy'B) - (y'AyB - y'By)(x'AxB - xAx'B)}{(xAyB - xByA)(xByA - xAyB)}$$

$$= \frac{(xAyB - xByA)(x'Ay'B - y'Ax'B)}{(xAyB - xByA)(xByA - xAyB)}$$

$$= \frac{(x'Ay'B - y'Ax'B)}{(xByA - xAyB)}$$

$$= \frac{Sur'}{Sur}$$

Given a surface Sur defined by a triangular mesh, and a projection $\pi$: Sur→$[0, 1]^2$. If we assume that $\pi$ is linear on each triangle, then we can compute efficiently $|\det J\pi(x)|$ for each x∈Sur. Give a triangle T we denote by s(T) the surface of T. Let Sur be a surface defined by a triangular mesh. Given v∈Sur, we denote by T(v) the triangle of Sur containing v. Let Sur'⊆Sur and let $\pi$: Sur→ $[0, 1]^2$ be an injection which is linear on each triangle of Sur. Denote by j: $[0, 1]^2 \to \mathbb{R}^+$ defined by $j(\pi(v))=s(T(v))/s(T(\pi(v)))$, and extended by j(x,y)=0 for (x,y) not ∈$\pi$(Sur). I.e. $j(\pi(v))$ is the ratio of the surface of the triangle containing x and the surface of the corresponding triangle on the projection.

Lemma 2. Let h: $[0, 1]^2 \to$ R. Then $$\int_{v \in Sur} h(\pi(v)) dv = \int_0^1 \int_0^1 h(x,y) j(x,y) dx dy$$

Proof. It is assumed that Sur is a triangular mesh, hence we can write Sur=$\coprod_i T_i$.

It follows that:

$$\int_{v \in Sur} h(\pi(v)) dv = \Sigma_i \int_{v \in Ti} h(\pi(v)) dv$$

$$= \Sigma_i \int_{(x,y) \in \pi(Ti)} h(x,y) |\det J\pi^{-1}(x,y)| dx dy$$

$$= \Sigma_i \int_{(x,y) \in \pi(Ti)} h(x,y) j(x,y) dx dy$$

$$= \int_{(x,y) \in \pi(Sur)} h(x,y) j(x,y) dx dy$$

$$= \int_{(x,y) \in [0,1]^2} h(x,y) j(x,y) dx dy$$

$$= \int_0^1 \int_0^1 h(x,y)(x,y) dx dy$$

Since f: Sur→R that we approximate $f(v) \approx \Sigma_k hk(\pi k(v)) fk(\pi k(v))$ It follows that:

$$\int_{v \in Sur} f(v) dv \approx \Sigma_k \int_{v \in Sur} hk(\pi k(v)) fk(\pi k(v)) dv$$

$$= \Sigma_k \int_0^1 \int_0^1 fk(x,y) hk(x,y) jk(x,y) dx dy$$

approximate the functions with n×n "bitmaps", $$h_k\left(\frac{i}{n}, \frac{j}{n}\right) \approx h_k(i, j)$$

and so on,
to obtain:

$$\int_{v \in Sur} f(v) dv \approx \frac{1}{n2} \sum_k \sum_{i=1}^n \sum_{j=1}^n fk(i,j) hk(i,j) jk(i,j)$$

It has been discovered that the application of the triangular mesh 216 of FIG. 2 to the left side image 202 of FIG. 2, the central image 204 of FIG. 2, and the right side image 206 of FIG. 2 can provide the average thresholds for uniformly identifying the acne pimples 409 of FIG. 4.

Figure 7:
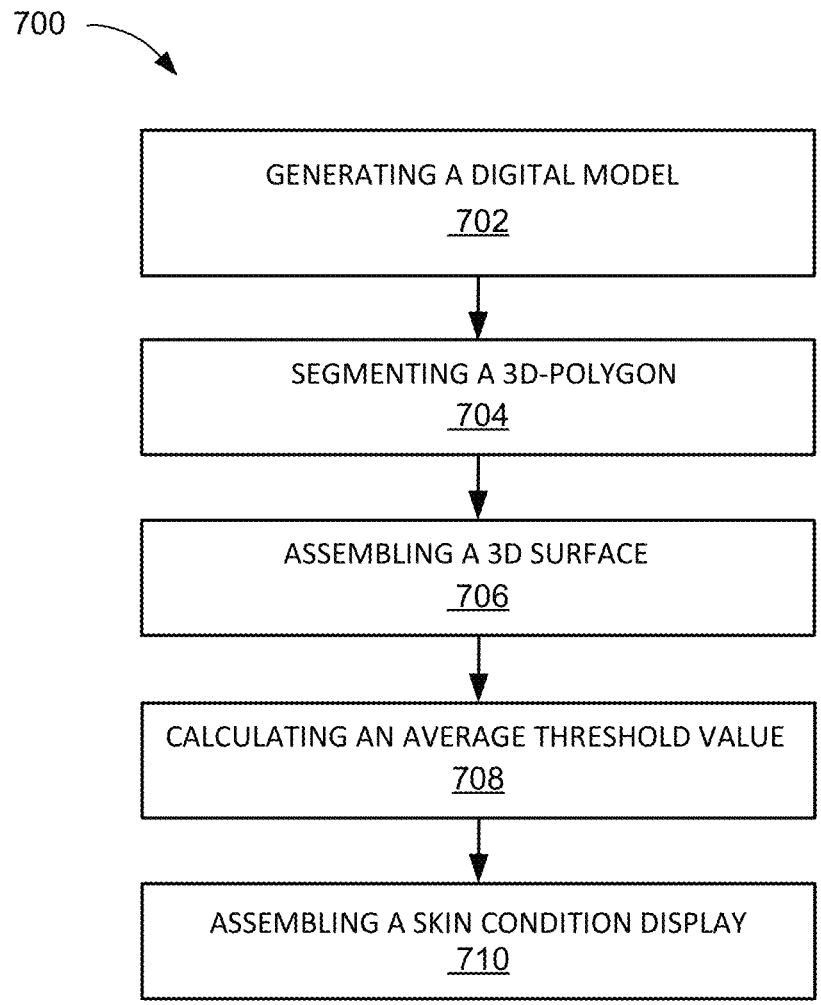
FIG. 7 is a flow chart of a method of operation of a compute system in an embodiment of the present invention.

Referring now to FIG. 7, therein is shown a flow chart of a method 700 of operation of a compute system 100 of FIG. 1 in an embodiment of the present invention. The method 700 includes: generating a digital model from a input image in a block 702; segmenting a 3D-polygon from the input image by applying a triangular mesh in a block 704; assembling a 3D surface, based on the digital model of a zone of interest from the 3D-polygon in a block 706; calculating an average threshold value of pixels within the zone of interest for identifying a condition over the 3D surface in a block 708; and assembling a skin condition display from analyzing by a skin artificial intelligence (AI) of the 3D surface for displaying on a device in a block 710.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of operation of a compute system comprising:
    generating a digital model from an input image;
    segmenting a 3D-polygon from the input image by applying a triangular mesh;
    assembling a 3D surface of a zone of interest from the 3D-polygon based on the digital model;
    generating a restricted heat map by applying the zone of interest to a heat map of the digital model to zero pixel values outside the zone of interest;
    calculating an average threshold value of pixels within the zone of interest and the restricted heat map for identifying a condition over the 3D surface; and assembling a skin condition display from analyzing by a skin artificial intelligence (AI) of the 3D surface for displaying on a device.

2. The method as claimed in claim 1 wherein generating the digital model includes segmenting the input image for analysis by a previously trained convolutional neural network.

3. The method as claimed in claim 1 wherein segmenting the 3D-polygons from the input image includes averaging the pixels of the 3D-polygons segmented by applying the triangular mesh.

4. The method as claimed in claim 1 wherein assembling the skin condition display includes assembling an acne score, an area of an acne, an estimated count, a 3D image sequence, and an identifying marker of the condition for display on the device.

5. The method as claimed in claim 1 wherein identifying the condition over the 3D surface includes identifying an acne type of an acne pimple from among a white head, a black head, a pustule, a cyst, a nodule, a papule, a comedone, and a discoloration.

6. The method as claimed in claim 1 wherein assembling the 3D surface includes compiling the zone of interest by matching the pixels of the 3D-polygons in a left side image, a central image, a right side image, or a combination thereof, and the digital model.

7. The method as claimed in claim 1 wherein calculating the average threshold value of the pixels for identifying the condition further comprising integrating the average threshold value from each of the 3D-polygon for a 3D image sequence of a first hemisphere image and a second hemisphere image.

8. A compute system comprising:
a control circuit, including a processor, configured to:
generate a digital model from an input image;
segment 3D-polygons from the input image by a triangular mesh;
assemble a 3D surface of interest from the 3D-polygons to match the digital model;
generate a restricted heat map by applying the zone of interest to a heat map of the digital model to zero pixel values outside the zone of interest; and
calculate an average threshold value of pixels within the zone of interest and the restricted heat map to identify a condition over the 3D surface; and
a communication circuit, coupled to the control circuit, configured to transfer a skin condition display from a skin artificial intelligence (AI) analysis of the 3D surface for displaying on a device.

9. The system as claimed in claim 8 wherein the control circuit is further configured to generate the digital model includes segmenting the input image by a previously trained convolutional neural network.

10. The system as claimed in claim 8 wherein the control circuit is further configured to segment the 3D-polygons from the input image by averaging the pixels of the 3D-polygons segmented by applying the triangular mesh.

11. The system as claimed in claim 8 wherein the control circuit is further configured to assemble the skin condition display to include an acne score, an area of an acne, an estimated count, a 3D image sequence, and an identifying marker of the condition assembled for display on the device.

12. The system as claimed in claim 8 wherein the control circuit is further configured to identify the condition over the 3D surface includes identifying an acne type of an acne pimple from among a white head, a black head, a pustule, a cyst, a nodule, a papule, a comedone, and a discoloration.

13. The system as claimed in claim 8 wherein the control circuit is further configured to assemble the 3D surface, including compiling a zone of interest by matching the pixels of the 3D-polygons in a left side image, a central image, a right side image, or a combination thereof, and the digital model.

14. The system as claimed in claim 8 wherein the control circuit is further configured to calculate the average threshold value of the pixels for identifying the condition further comprising integrating the average threshold value from the 3D-polygon for a 3D image sequence of a first hemisphere image and a second hemisphere image.

15. A non-transitory computer readable medium including instructions executable by a control circuit for a compute system for performing functions comprising:
generating a digital model from an input image;
segmenting 3D-polygons from the input image by applying a triangular mesh;
assembling a 3D surface of a zone of interest from the 3D-polygon matching the digital model;
generating a restricted heat map by applying the zone of interest to a heat map of the digital model to zero pixel values outside the zone of interest;
calculating an average threshold value of pixels within the zone of interest and the restricted heat map for identifying a condition over the 3D surface; and
assembling a skin condition display from analyzing by a skin artificial intelligence (AI) of the 3D surface for displaying on a device.

16. The non-transitory computer readable medium as claimed in claim 15 wherein generating the digital model includes segmenting the input image for analysis by a previously trained convolutional neural network.

17. The non-transitory computer readable medium as claimed in claim 15 wherein segmenting the 3D-polygons from the input image includes averaging the pixels of the 3D-polygons segmented by applying the triangular mesh.

18. The non-transitory computer readable medium as claimed in claim 15 further comprising assembling the skin condition display includes assembling an acne score, an area of an acne, an estimated count, a 3D image sequence, and an identifying marker of the condition for display on the device.

19. The non-transitory computer readable medium as claimed in claim 15 wherein identifying the condition over the 3D surface includes identifying an acne type of an acne pimple from among a white head, a black head, a pustule, a cyst, a nodule, a papule, a comedone, and a discoloration.

20. The non-transitory computer readable medium as claimed in claim 15 assembling the 3D surface includes compiling a zone of interest by matching the pixels of the 3D-polygons in a left side image, a central image, a right side image, or a combination thereof, and the digital model.

* * * * *